US008686126B2

(12) United States Patent
Bozdayi

(10) Patent No.: US 8,686,126 B2
(45) Date of Patent: Apr. 1, 2014

(54) HBV DRUG RESISTANCE METHODS

(75) Inventor: Abdurrahman Mithat Bozdayi, Golbasi-Ankara (TR)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 13/553,214

(22) Filed: Jul. 19, 2012

(65) Prior Publication Data

US 2013/0040284 A1 Feb. 14, 2013

Related U.S. Application Data

(63) Continuation of application No. 10/509,094, filed as application No. PCT/EP02/03559 on Mar. 29, 2002, now Pat. No. 8,278,432.

(51) Int. Cl.
*C07H 21/04* (2006.01)
*C12Q 1/70* (2006.01)
*C12Q 1/68* (2006.01)
*G01N 33/53* (2006.01)

(52) U.S. Cl.
USPC ............. 536/24.32; 536/33; 435/5; 435/6.11; 435/7.2

(58) Field of Classification Search
None
See application file for complete search history.

(56) References Cited

U.S. PATENT DOCUMENTS

| 6,555,311 | B1 | 4/2003 | Locarnini |
| 2003/0124096 | A1 | 7/2003 | Locarnini |
| 2006/0165725 | A1 | 7/2006 | Bozdayi |
| 2006/0234212 | A1 | 10/2006 | Bozdayi |
| 2007/0042356 | A1 | 2/2007 | Schildgen |

FOREIGN PATENT DOCUMENTS

| WO | WO 94/26904 | 11/1994 |
| WO | 97/40193 | 10/1997 |
| WO | WO 98/21317 | 5/1998 |
| WO | WO 00/58477 | 10/2000 |
| WO | WO 00/61758 | 10/2000 |
| WO | 03/066841 | 8/2003 |
| WO | 03/087351 | 10/2003 |
| WO | 2004/031224 | 4/2004 |

OTHER PUBLICATIONS

Alexopoulou A et al, J General Virology (1996), vol. 3, pp. 173-181, "Whole genome analysis of hepatitis B virus from four cases of fulminant hepatitis: genetic variability and its potential role in disease pathogenicity" Table 3.
Aye et al, "Hepatitis B Virus Polymerase Mutations During Famciclovir Therapy in Patients Following Liver Transplantation", Hepatology vol. 24, No. 4, Pt.2, Abstract 633, Sep. 1996.
Aye et al, "Hepatitis B Virus polymerase mutations during antiviral therapy in a patient following liver transplantation", Journal of Hepatology, 1997; 26: 1148-1153.
Bartholomeusz et al, "Mutations in the hepatitis B virus polymerase gene that are associated with resistance to famciclovir and lamivudine", 1997, International Antiviral News , vol. 5, No. 8, 123-124.
Bartholomew, "Hepatitis-B-virus resistance to lamivudine given for recurrent infection after orthotopic liver transplantation", (Lancet 349: 20-22, Jan. 1997).
Bowyer S et al, J General Virology (1997), vol. 78, pp. 1719-1729, "A unique segment of the hepatitis B virus group A genotype identified in isolates from South Africa" Figure 5.
Carman et al, "Vaccine-induced escape mutant . . . ", The Lancet, vol. 336, 1990 (8711) pp. 325-329.
Carman, "The clinical significance of surface antigen variants . . . ", Journal of Viral Hepatitis, 1997. 4 (Suppl. 1) 11-20.
Chenault, "Patterns of nucleotide sequence variation among cauliflower mosaic virus isolates", (Biochimie 76:3-8, 1994).
de Man et al, "The sequential occurrence of viral mutations in a liver transplant recipient re-infected with hepatitis B: hepatitis B immune globuline escape, famciclovir non-respnse, followed by lamivudine resistance resulting in graft loss", Journal of Hepatology, 1998; 29: 669-675.
Fischer et al, "Generation of Duck Hepatitis B Virus Polymerase Mutants through Site-Directed Mutagenesis Which Demonstrate Resistance to Lamivudine [(−)-β-L-2',3'-Dideoxy-3'-Thiacytidine] In Vitro", Antimicrobial Agents & Chemotherapy 40: 1957-1960, Aug. 1996.
Fujii et al, "Gly$^{145}$ to Arg Substitution in HBs Antigen of . . . ", Biochemical and Biophysical Research Communications, vol. 184, No. 3, May 15, 1992, pp. 1152-1157.
Ho et al, "A Family Cluster of an Immune Escape Variant of Hepatitis B Virus Infecting a Mother and Her Two Fully Immunized Children", Clinical and Diagnostic Laboratory Immunology, 1995, vol. 2, No. 6, pp. 760-762.
Horikita M et al, J Medical Virology (1994), vol. 44(1), pp. 96-103, "Differences in the entire nucleotide sequence between hepatitis B virus genomes from carriers positive for antibody to hepatitis B e antigen with and without active disease" Table IV.
Ling ("Selection of mutations in hepatitis B virus polymerase during therapy of transplant recipients with lamivudine" Hepatology 24(3): 711-713, Sep. 1996).
Ni F et al, Research in Virology (1995), vol. 146(6), pp. 397-407, "A new immune escape mutant of hepatitis B virus with an Asp to Ala substitution in aa144 of the envelope major protein" Figure 3.

(Continued)

*Primary Examiner* — Nicole Kinsey White
(74) *Attorney, Agent, or Firm* — Nixon & Vanderhye P.C.

(57) ABSTRACT

New polymorphisms in the nucleic acid sequences of the DNA polymerase/reverse transcriptase open reading frame and viral surface antigen open reading frame of the hepatitis B virus are reported. In particular, the present invention relates to the mutation YMDD→YSDD in the HBV reverse transcriptase domain and to the W196V mutation in the small HBV viral surface antigen. Said polymorphisms are affecting the detection of drug resistance mutations by genotypic methods and diagnostic kits based thereon. The present invention relates to methods and diagnostic kits for detection of a HBV virus comprising said nucleic acid polymorphisms. In particular, those methods utilizing oligonucleotides capable of hybridizing to said HBV nucleic acid polymorphisms are envisaged.

4 Claims, 4 Drawing Sheets

(56) References Cited

OTHER PUBLICATIONS

Figure 1:
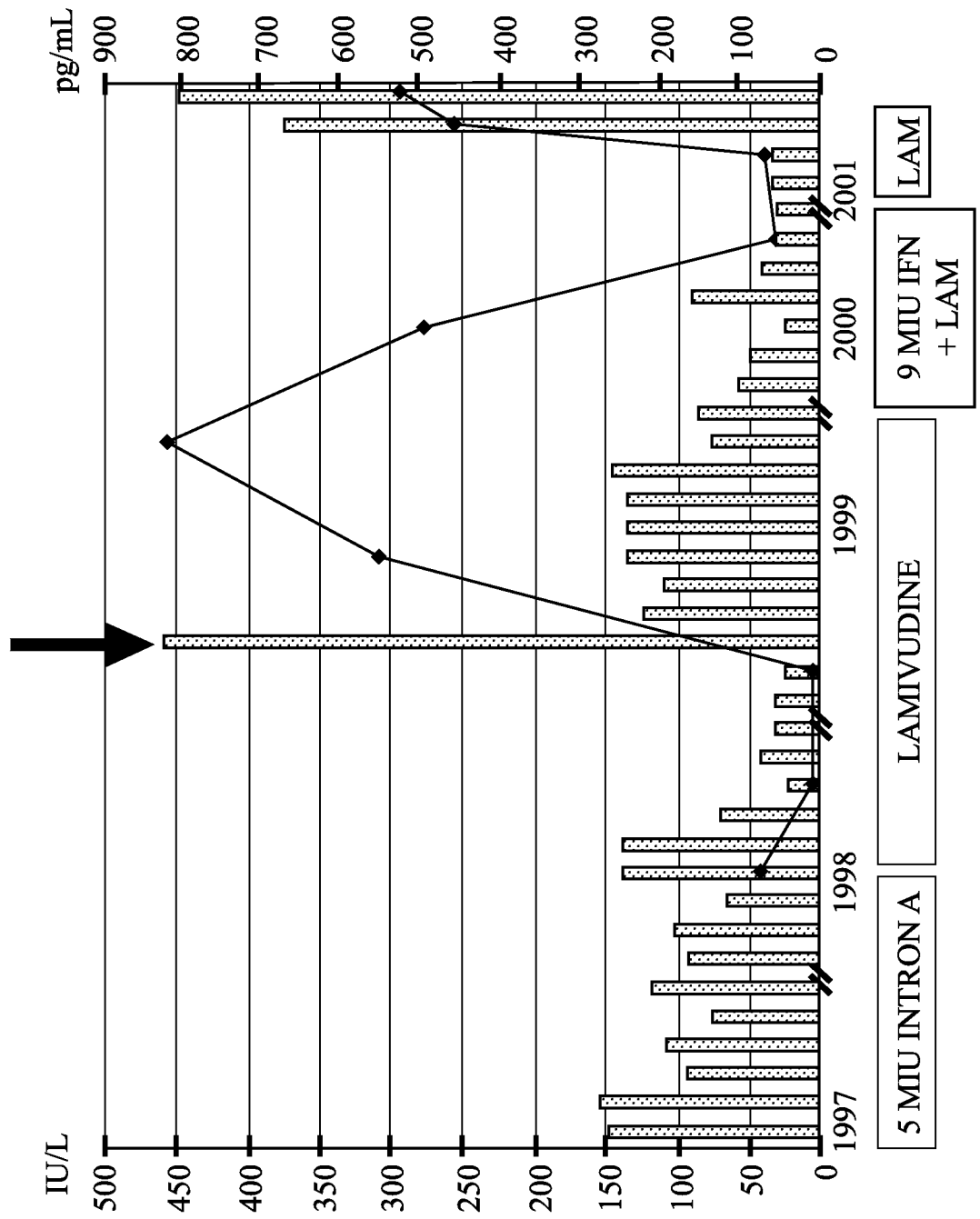

Norder, "Molecular basis of hepatitis B virus serotype variations within the four major subtypes", (Virology 198: 489-503, 1994).

Norder et al, "Molecular basis of hepatitis B virus serotype variations within the four major subtypes", Journal of General Virology 1992, vol. 73, pp. 3141-3145.

Norder H et al, J General Virology (1992), vol. 73(5), pp. 1201-1208, "Comparison of the amino acid sequences of nine different scrotypes of hepatitis B surface antigen and genomic classification of the corresponding hepatitis B strains" Figure 3.

Norder H et al, J General Virology (1993), vol. 74, pp. 1341-1348, "Genetic relatedness of hepatitis B viral strains of diverse geographical origin and natural variations in the primary structure of the surface antigen" Figure 2.

Okamoto F et al, J. General Virology (1988), vol. 69, pp. 2575-2583, "Typing hepatitis B virsu by homology in nucleotide sequence: comparison of surface antigen subtypes" Figure 1.

Ono Y et al, Nucleic Acids Research(1983), vol. 11(6), pp. 1747-1757, "The complete nucleotide of the cloned hepatitis B virus DNA; subtype adr and adw"Figure 2 and 3.

Pasek M et al, Nature(1979), vol. 282, pp. 575-579, "Hepatitis B virus genes and their expression in E. coli" Figure 2.

Perrillo et al, "Adefovir Dipivoxil Added to Ongoing Lamivudine in Chronic Hepatitis B with YMDD Mutant Hepatitis B Virus", Gastroenterology 2004; 126:81-90.

Poch et al, "Identification of four conserved motifs among the RNA-dependent polymerase encoding elements" EMBO Journal 8: 3867-3874, 1989.

Ren H et al, "Expression of 12 antibody escape mutants of hepatitis B virus surface antigen gene in mammalian cell by using an Epstein-Barr based vector", Chung Hua I Hseuh Tsa Chih 1995 75(7) pp. 396-398 (PubMed English Abstract PMID 7553156).

Rivkina M et al, Gene (1988), vol. 64, pp. 285-296, "Nucleotide sequence of integrated hepatitis B virus DNA and human flanking regions in the genome of the PLC/PRF/5 cell line" Figure 5.
Stuyver et al, "Nomenclature for Antiviral-Resistant Human Hepatitis B Virus Mutations in the Polymerase Region", Hepatology 2001; 33:751-757.
Tipples ("Mutation in HBV RNA-dependent DNA polymerase confers resistance to lamivudine in vivo" Hepatology 24(3): 714-717, Sep. 1996).
Uchida T et al, J General Virology (1995), vol. 45, pp. 247-252, Complete nucleotide sequences and the characteristics of two hepatitis B virus mutants causing serologically negtive acute or chronic hepatitis B: p. 249.
Uchida,T. et al. Gen Bank Accession No. D50489, Title: "Direct Submission" Submitted (May 8, 1995) http://www.ncbi.nlm.nih.gov/entrez/viewer.fcgi?db=nuccore&id=807711.
Vaudin M et al, J. General Virology (1988), vol. 69, pp. 1383-1389, "The complete nucleotide sequence of the genome of a hepatitis B virus isolated from a naturally infected chimpanzee" Figure 1.
Wang GT et al, "Sequencing of hepatitis B virus DNA fragment coding major HBsAg of escape mutant", Chung Hua I Hseuh Tsa Chih Jun. 1994 74(6) pp. 355-357, 391 (PubMed English Abstract PMID 7994645).
Weiss et al, "The HBV-Producing Cell Line HepG2-4A5: A new in vitro system for studying the regulation of HBV replication and for screening anti-hepatitis B virus drugs", Virology 216:214-218, Feb. 1, 1996.
Werle et al "Evolution of hepatitis B virus load and viral genome sequence during adefovir dipivoxil therapy" 2004, Journal of Viral Hepatitis, vol. 11, No. 1, pp. 74-83.
Yamamoto et al, "Naturally Ocurring Escape Mutants of Hepatitis B Virus with . . . ", Journal of Virology, vol. 68, No. 4, Apr. 1994, pp. 2671-2676.
Blum, "Variants of Hepatitis B, C and D Viruses: Molecular Biology and Clinical Significance", Digestion (1995); 56:85-95.
Kidd-Ljunggren, "Variability in Hepatitis B Virus DNA: Phylogenetic, Epidemiological and Clinical Implications", Scand J Infect Dig 28:111-116 (1996).
Kan Tan Sui, "Escape Mutants of HBs" (1993), 27(4), pp. 555-562.
H. Uetake Ed., Virology, $4^{th}$ Ed., ver.1, Rikougaku-sha (publ.), Jul. 10, 2002, p. 452 (in Japanese).
Aoyama & Partners letter dated Feb. 15, 2007, relating to Japanese Patent Application No. 521944/1998 (4 pages).
Aoyama & Partners letter dated Jan. 25, 2007, relating to Japanese Patent Application No. 521944/1998 (2 pages).
Aoyama & Partners letter dated Jul. 23, 2007, relating to Japanese Patent Application No. 521944/1998 (1 page) with English translation of amended claims (2 pages) and Amendment filed Jul. 19, 2007, in response to Official Action (11 pages).
Yan, L. et al, Accession No. Q9IF40, submitted (Jun. 2000), title: "Direct Submission", http://www.ncbi.nlm.nih.gov.
Stoll-Becker et al, "Transcription of Hepatitis B Virus in Peripheral Blood Mononuclear Cells from Persistently Infected Patients", Journal of Virology, Jul. 1997, vol. 71, No. 7, pp. 5399-5407.
Gerner et al, "Hepatitis B Virus Core Promoter Mutations in Children with Multiple Anti-HBe/HBeAg Reactivations Result in Enhanced Promoter Activity", Journal of Medical Virology 59:415-423 (1999).
Niesters et al, "Identification of a new variant in the YMDD motif of the hepatitis B virus polymerase gene selected during lamivudine therapy", J. Med. Microbiol., vol. 51 (2002), 695-699.
Wakefield et al, "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome", Journal of Virology, Nov. 1992, vol. 66, No. 11, pp. 6806-6812.
Torresi et al, "Restoration of Replication Phenotype of Lamivudine-Resistant Hepatitis B Virus Mutants by Compensatory Changes in the "Fingers" Subdomain of the Viral Polymerase Selected as a Consequence of Mutations in the Overlapping S Gene", Virology 299, 88-99 (2002).
Delaney et al, "Phenylpropenamide Derivatives AT-61 and AT-130 Inhibit Replication of Wild-Type and Lamivudine-Resistant Strains of Hepatitis B Virus In Vitro", Antimicrobial Agents and Chemotherapy, Sep. 2002, vol. 46, No. 9, pp. 3057-3060.
Delaney et al, "Resistance of hepatitis B virus to antiviral drugs: current aspects and directions for future investigation", Antiviral Chemistry & Chemotherapy 12:1-35 (2001).
Gaillard et al, "Kinetic Analysis of Wild-Type and YMDD Mutant Hepatitis B Virus Polymerases and Effects of Deoxyribonucleotide Concentrations on Polymerase Activity", Antimicrobial Agents and Chemotherapy, Apr. 2002, vol. 46, No. 4, pp. 1005-1013.
Han et al, "YMDD Motif Mutants in Hepatitis B Virus Polymerase during Lamivudine Therapy", Korean J. Genetics 24(2):219-226 (Jun. 2002).
Tatti et al, "Mutations in the conserved woodchuck hepatitis virus polymerase FLLA and YMDD regions conferring resistance to lamivudine", Antiviral Research 55 (2002) 141-150.
Stuyer et al, "Nomenclature for antiviral-resistant human hepatitis B virus mutations in the polymerase region", Hepatology, Mar. 2001; 33(3):751-7.
Bozdayi et al, "A new mutation pattern (YMDD ->YSDD) in YMDD motif of HBV—DNA polymerase gene in chronic B hepatitis infection resistant to lamivudine treatment", Journal of Hepatology, 2001, 34(1):162. Meeting Abstract.
Petzold et al., GenBank Accession No. AJ131956, Submitted Jan. 5, 1999.
Allen et al, "Identification and Characterization of Mutations in Hepatitis B Virus Resistant to Lamivudine", Hepatology, 1998, 27:1670-1677.
Zaaijer et al, "Comparison of Methods for Detection of Hepatitis B Virus DNA", Journal of Clinical Microbiology, Sep. 1994, 32(9):2088-2091.
Rule 132 Declaration of Abdurrahman Bozdayi dated Jun. 26, 2007, USPTO date-stamped Aug. 27, 2007, filed in U.S. Patent Application of Bozdayi, U.S. Appl. No. 10/509,094.

```
RT              100         110         120
                 |           |           |
HBVD  RT   AMPHLLVGSSGLSRYVARLSSNSRIFNYQ
p7RT       .............................

RT              130         140         150
                 |           |           |
HBVD  RT   HGTMQNLHDSCSRNLYVSLLLLYQTFGRK
P7RT       .............................

RT              160         170         180
                 |           |           |
HBVD  RT   LHLYSHPIILGFRKIPMGVGLSPFL[L]AQF
P7RT       ........................[M]...

RT              190         200         210
                 |           |           |
HBVD  RT   TSAICSVVRRAFPHCLAFSY[M]DDVVLGAK
P7RT       ....................[S].......

RT              220         230         240
                 |           |           |
HBVD  RT   SVQHLESLFTAVTNFLLSLGIHLNPNKTK
P7RT       .............................

RT              250   256
                 |     |
HBVD  RT   RWGYSLHFMGYVIGC
P7RT       ...............

HBVD RT = SEQ ID NO:1
P7RT = SEQ ID NO:4
```

FIGURE 2

```
S              90                  100                 110
               |                   |                   |
HBVD  S    L C L I F L L V L L D Y Q G M L P V C P L I P G S S T T S
P7S        . . . . . . . . . . . . . . . . . . . . . . . . . . . .

120                 130                 140
               |                   |                   |
HBVD  S    T G P C R T C T T P A Q G T S M Y P S C C C T K P S D G N
P7S        . . . . . . . . . . . . . . . . . . . . . . . . . . . .

150                 160                 170
               |                   |                   |
HBVD  S    C T C I P I P S S W A F G K F L W E W A S A R F S W L S L
P7S        . . . . . . . . . . . . . . . . . . . . . . . . . . . .

180                 190                 200
               |                   |                   |
HBVD  S    L V P F V Q W F V G L S P T V W L S V I W M M W Y W G P S
P7S        . . . . . . . . . . . . . . . . . . . . . V . . . . . . .

210                 220                 226
               |                   |                   |
HBVD  S    L Y S I L S P F L P L L P I F F C L W V Y I
P7S        . . . . . . . . . . . . . . . . . . . . . .
```

HBVD S = SEQ ID NO:2
P7S = SEQ ID NO:5

FIGURE 3

```
HBVD    420  gctatgcctcatcttcttgttggttcttctggactatcaa
P7           ........................................

HBVD    460  ggtatgttgcccgtttgtcctctaattccaggatcttcaa
P7           ........................................

HBVD    500  ctaccagcacgggaccatgcagaacctgcacgactcctgc
P7           ........................................

HBVD    540  tcaaggaacctctatgtatccctcctgttgctgtaccaaa
P7           ........................................

HBVD    580  ccttcggacggaaattgcacctgtattcccatcccatcat
P7           ........................................

HBVD    620  cctgggctttcggaaaattcctatgggagtgggcctcagc
P7           ........................................

HBVD    660  ccgtttctc c tggctcagtttactagtgccatttgttcag
P7           ........ a ...............................

HBVD    700  tggttcgtagggctttcccccactgtttggctttcagtta
P7           ........................................

HBVD    740  ta t g gatgatgtggtattgggggccaagtctgtacagcat
P7           .. g t ..................................

HBVD    780  cttgagtccctttttaccgctgttaccaatttttctt c tgt
P7           .................................. t ...

HBVD    820  ctttgggtatacatttaaaccctaacaaaacaaaaagatg
P7           ........................................

HBVD    860  gggttactctttacatttcatggg c tatgtcattggatgt
P7           ....................... g ...............

HBVD = SEQ ID NO:3
P7 = SEQ ID NO:6
```

FIGURE 4

SEQUENCE LISTING

```
<160> NUMBER OF SEQ ID NOS: 16

<210> SEQ ID NO 1
<211> LENGTH: 160
<212> TYPE: PRT
<213> ORGANISM: hepatitis B virus

<400> SEQUENCE: 1

Ala Met Pro His Leu Leu Val Gly Ser Ser Gly Leu Ser Arg Tyr Val
1               5                   10                  15

Ala Arg Leu Ser Ser Asn Ser Arg Ile Phe Asn Tyr Gln His Gly Thr
            20                  25                  30

Met Gln Asn Leu His Asp Ser Cys Ser Arg Asn Leu Tyr Val Ser Leu
        35                  40                  45

Leu Leu Leu Tyr Gln Thr Phe Gly Arg Lys Leu His Leu Tyr Ser His
    50                  55                  60

Pro Ile Ile Leu Gly Phe Arg Lys Ile Pro Met Gly Val Gly Leu Ser
65                  70                  75                  80

Pro Phe Leu Leu Ala Gln Phe Thr Ser Ala Ile Cys Ser Val Val Arg
```

```
                    85                  90                  95
Arg Ala Phe Pro His Cys Leu Ala Phe Ser Tyr Met Asp Asp Val Val
                100                 105                 110

Leu Gly Ala Lys Ser Val Gln His Leu Glu Ser Leu Phe Thr Ala Val
            115                 120                 125

Thr Asn Phe Leu Leu Ser Leu Gly Ile His Leu Asn Pro Asn Lys Thr
        130                 135                 140

Lys Arg Trp Gly Tyr Ser Leu His Phe Met Gly Tyr Val Ile Gly Cys
145                 150                 155                 160

<210> SEQ ID NO 2
<211> LENGTH: 137
<212> TYPE: PRT
<213> ORGANISM: hepatitis B virus

<400> SEQUENCE: 2

Leu Cys Leu Ile Phe Leu Leu Val Leu Leu Asp Tyr Gln Gly Met Leu
1               5                   10                  15

Pro Val Cys Pro Leu Ile Pro Gly Ser Ser Thr Thr Ser Thr Gly Pro
                20                  25                  30

Cys Arg Thr Cys Thr Thr Pro Ala Gln Gly Thr Ser Met Tyr Pro Ser
            35                  40                  45

Cys Cys Cys Thr Lys Pro Ser Asp Gly Asn Cys Thr Cys Ile Pro Ile
        50                  55                  60

Pro Ser Ser Trp Ala Phe Gly Lys Phe Leu Trp Glu Trp Ala Ser Ala
65                  70                  75                  80

Arg Phe Ser Trp Leu Ser Leu Val Pro Phe Val Gln Trp Phe Val Gly
                85                  90                  95

Leu Ser Pro Thr Val Trp Leu Ser Val Ile Trp Met Met Trp Tyr Trp
                100                 105                 110

Gly Pro Ser Leu Tyr Ser Ile Leu Ser Pro Phe Leu Pro Leu Leu Pro
            115                 120                 125

Ile Phe Phe Cys Leu Trp Val Tyr Ile
        130                 135

<210> SEQ ID NO 3
<211> LENGTH: 480
<212> TYPE: DNA
<213> ORGANISM: hepatitis B virus

<400> SEQUENCE: 3
gctatgcctc atcttcttgt tggttcttct ggactatcaa ggtatgttgc ccgtttgtcc      60
tctaattcca ggatcttcaa ctaccagcac gggaccatgc agaacctgca cgactcctgc     120
tcaaggaacc tctatgtatc cctcctgttg ctgtaccaaa ccttcggacg gaaattgcac     180
ctgtattccc atcccatcat cctgggcttt cggaaaattc ctatgggagt gggcctcagc     240
ccgtttctcc tggctcagtt tactagtgcc atttgttcag tggttcgtag gctttcccc      300 cactgtttgg ctttcagtta tatggatgat gtggtattgg gggccaagtc tgtacagcat     360
cttgagtccc tttttaccgc tgttaccaat tttcttctgt ctttgggtat acatttaaac     420
cctaacaaaa caaaaagatg gggttactct ttacatttca tgggctatgt cattggatgt     480

<210> SEQ ID NO 4
<211> LENGTH: 160
<212> TYPE: PRT
<213> ORGANISM: hepatitis B virus

<400> SEQUENCE: 4
```

Ala Met Pro His Leu Leu Val Gly Ser Gly Leu Ser Arg Tyr Val
1               5                   10                  15

Ala Arg Leu Ser Ser Asn Ser Arg Ile Phe Asn Tyr Gln His Gly Thr
            20                  25                  30

Met Gln Asn Leu His Asp Ser Cys Ser Arg Asn Leu Tyr Val Ser Leu
        35                  40                  45

Leu Leu Leu Tyr Gln Thr Phe Gly Arg Lys Leu His Leu Tyr Ser His
    50                  55                  60

Pro Ile Ile Leu Gly Phe Arg Lys Ile Pro Met Gly Val Gly Leu Ser
65                  70                  75                  80

Pro Phe Leu Met Ala Gln Phe Thr Ser Ala Ile Cys Ser Val Val Arg
                85                  90                  95

Arg Ala Phe Pro His Cys Leu Ala Phe Ser Tyr Ser Asp Asp Val Val
            100                 105                 110

Leu Gly Ala Lys Ser Val Gln His Leu Glu Ser Leu Phe Thr Ala Val
        115                 120                 125

Thr Asn Phe Leu Leu Ser Leu Gly Ile His Leu Asn Pro Asn Lys Thr
    130                 135                 140

Lys Arg Trp Gly Tyr Ser Leu His Phe Met Gly Tyr Val Ile Gly Cys
145                 150                 155                 160

<210> SEQ ID NO 5
<211> LENGTH: 137
<212> TYPE: PRT
<213> ORGANISM: hepatitis B virus

<400> SEQUENCE: 5

Leu Cys Leu Ile Phe Leu Leu Val Leu Leu Asp Tyr Gln Gly Met Leu
1               5                   10                  15

Pro Val Cys Pro Leu Ile Pro Gly Ser Ser Thr Thr Ser Thr Gly Pro
            20                  25                  30

Cys Arg Thr Cys Thr Thr Pro Ala Gln Gly Thr Ser Met Tyr Pro Ser
        35                  40                  45

Cys Cys Cys Thr Lys Pro Ser Asp Gly Asn Cys Thr Cys Ile Pro Ile
    50                  55                  60

Pro Ser Ser Trp Ala Phe Gly Lys Phe Leu Trp Glu Trp Ala Ser Ala
65                  70                  75                  80

Arg Phe Ser Trp Leu Ser Leu Val Pro Phe Val Gln Trp Phe Val Gly
                85                  90                  95

Leu Ser Pro Thr Val Trp Leu Ser Val Ile Val Met Met Trp Tyr Trp
            100                 105                 110

Gly Pro Ser Leu Tyr Ser Ile Leu Ser Pro Phe Leu Pro Leu Leu Pro
        115                 120                 125

Ile Phe Phe Cys Leu Trp Val Tyr Ile
    130                 135

<210> SEQ ID NO 6
<211> LENGTH: 480
<212> TYPE: DNA
<213> ORGANISM: hepatitis B virus

<400> SEQUENCE: 6
gctatgcctc atcttcttgt tggttcttct ggactatcaa ggtatgttgc ccgtttgtcc     60
tctaattcca ggatcttcaa ctaccagcac gggaccatgc agaacctgca cgactcctgc    120
tcaaggaacc tctatgtatc cctcctgttg ctgtaccaaa ccttcggacg gaaattgcac    180

-continued

```
ctgtattccc atcccatcat cctgggcttt cggaaaattc ctatgggagt gggcctcagc    240
ccgtttctca tggctcagtt tactagtgcc atttgttcag tggttcgtag ggctttcccc    300
cactgtttgg ctttcagtta tagtgatgat gtggtattgg gggccaagtc tgtacagcat    360
cttgagtccc tttttaccgc tgttaccaat tttcttttgt ctttgggtat acatttaaac    420
cctaacaaaa caaaaagatg gggttactct ttacatttca tggggtatgt cattggatgt    480

<210> SEQ ID NO 7
<211> LENGTH: 31
<212> TYPE: DNA
<213> ORGANISM: artificial sequence
<220> FEATURE:
<223> OTHER INFORMATION: synthetic probe or primer

<400> SEQUENCE: 7
cacctgcagc ctcatttgt gggtcaccat a                                    31

<210> SEQ ID NO 8
<211> LENGTH: 35
<212> TYPE: DNA
<213> ORGANISM: artificial sequence
<220> FEATURE:
<223> OTHER INFORMATION: synthetic probe or primer

<400> SEQUENCE: 8
cataagcttc acaattcgtt gacatacttt ccaat                               35

<210> SEQ ID NO 9
<211> LENGTH: 31
<212> TYPE: DNA
<213> ORGANISM: artificial sequence
<220> FEATURE:
<223> OTHER INFORMATION: synthetic probe or primer

<400> SEQUENCE: 9
gtgctgcagt ttgtgggtca ccatattctt g                                   31

<210> SEQ ID NO 10
<211> LENGTH: 32
<212> TYPE: DNA
<213> ORGANISM: artificial sequence
<220> FEATURE:
<223> OTHER INFORMATION: synthetic probe or primer

<400> SEQUENCE: 10
gacaagcttt tgacatactt tccaatcaat ag                                  32

<210> SEQ ID NO 11
<211> LENGTH: 12
<212> TYPE: PRT
<213> ORGANISM: artificial sequence
<220> FEATURE:
<223> OTHER INFORMATION: Tag 100 epitope

<400> SEQUENCE: 11

Glu Glu Thr Ala Arg Phe Gln Pro Gly Tyr Arg Ser
1               5                   10

<210> SEQ ID NO 12
<211> LENGTH: 10
<212> TYPE: PRT
<213> ORGANISM: artificial sequence
<220> FEATURE:
<223> OTHER INFORMATION: c-myc epitope

<400> SEQUENCE: 12
```

```
Glu Gln Lys Leu Ile Ser Glu Glu Asp Leu
1               5                   10

<210> SEQ ID NO 13
<211> LENGTH: 7
<212> TYPE: PRT
<213> ORGANISM: artificial sequence
<220> FEATURE:
<223> OTHER INFORMATION: FLAG-epitope

<400> SEQUENCE: 13

Asp Tyr Lys Asp Asp Asp Lys
1               5

<210> SEQ ID NO 14
<211> LENGTH: 9
<212> TYPE: PRT
<213> ORGANISM: artificial sequence
<220> FEATURE:
<223> OTHER INFORMATION: HA epitope

<400> SEQUENCE: 14

Tyr Pro Tyr Asp Val Pro Asp Tyr Ala
1               5

<210> SEQ ID NO 15
<211> LENGTH: 12
<212> TYPE: PRT
<213> ORGANISM: artificial sequence
<220> FEATURE:
<223> OTHER INFORMATION: protein C epitope

<400> SEQUENCE: 15

Glu Asp Gln Val Asp Pro Arg Leu Ile Asp Gly Lys
1               5                   10

<210> SEQ ID NO 16
<211> LENGTH: 11
<212> TYPE: PRT
<213> ORGANISM: artificial sequence
<220> FEATURE:
<223> OTHER INFORMATION: VSV epitope

<400> SEQUENCE: 16

Tyr Thr Asp Ile Glu Met Asn Arg Leu Gly Lys
1               5                   10
```

HBV DRUG RESISTANCE METHODS

This application is a continuation of Ser. No. 10/509,094 (now U.S. Pat. No. 8,278,432), filed Oct. 22, 2004 (published as US 2006-0165725 A1), which is a U.S. national phase of International Application No. PCT/EP02/03559, filed Mar. 29, 2002, which designated the U.S., the entire contents of each of which are hereby incorporated by reference.

FIELD OF THE INVENTION

The present invention relates to detection of hepatitis B viruses and/or of HBV nucleic acid polymorphisms in a biological sample. More specifically, said HBV nucleic acid polymorphisms occur in the open reading frame encoding the polymerase/reverse transcriptase of the HBV virus and in the corresponding part of the overlapping open reading frame encoding the HBV viral surface antigen. In particular, the current invention covers a new lamivudine-induced mutation YMDD→YSDD in the HBV polymerase. The current invention further concerns methods for reliable detection in a biological sample of HBV strains comprising said DNA nucleic acid polymorphisms as well as oligonucleotides used thereto. The invention further relates to vectors comprising said HBV nucleic acid polymorphisms as well as to methods testing the sensitivity to antiviral compounds of HBV variants comprising said HBV nucleic acid polymorphisms.

Throughout the invention as described below various publications are referenced. The contents of said publications are hereby incorporated by reference into the current application. Said publications are meant to describe more fully the art to which the current invention pertains.

BACKGROUND OF THE INVENTION

The hepatitis B virus (HBV) belongs to the Hepadnaviridae, a group of hepatotropic DNA viruses. This group of viruses comprises not only human or primate HBV, but also duck-, woodchuck-, ground squirrel-, tree squirrel- and heron HBV. The genome of human HBV consists of a partially double-stranded ~3.2 kb DNA molecule. The HBV genome contains four partly overlapping open reading frames (ORFs) being (i) the preC/C ORF encoding the secreted e antigen (HBeAg) and nucleocapsid core protein (HBcAg), respectively; (ii) the P ORF encoding the viral polymerase/reverse transcriptase; (iii) the preS1/preS2/S ORF encoding the viral envelope proteins, large, middle and small s antigen (HBsAg), respectively; and (iv) the X ORF encoding a transcriptional trans-activator protein.

The HBV envelope comprises three related glycoproteins, termed hepatitis B surface antigens (HBsAg), which are the product of the S gene: 1) the "small" transmembrane protein, Also termed major protein or small S-protein, composed of 226 amino acids (aa), 2) the "middle" protein which comprises the small S-protein and 55 additional aa at the N-terminus corresponding to the pre-S2 region of the S gene, and 3) the "large" protein composed of 389 (genotype D), 399 (genotypes E and G) or 400 (genotypes A to C and F) aa corresponding to the following regions: S+pre-S2+pre-S1 (108-119 N-terminal aa) (Robinson et al., 1987; Heermann et al., 1984). The envelope of HDV (hepatitis delta virus) is also entirely derived from HBV and consists predominantly of small HBsAg, 5-10% of middle HBsAg and no or less then 1% of large HBsAg (Bonino et al., 1986).

Hepatitis B viruses exhibit a large genetic variability in their genomes, with currently 7 HBV genotypes (A to G) being recognized (Stuyver et al., 2001; Stuyver et al., 2000). Furthermore, hepatitis B viruses do not circulate in infected individuals as homogeneous populations of identical viral particles, but rather as a pool of genetically distinct but closely related variants. This genetic variation confers a significant advantage to the virus, as the simultaneous presence of multiple variant genomes and the high rate at which new variants are generated allow rapid selection of mutants better suited to survive in new environmental conditions. Mutations in the HBV polymerase and their clinical relevance are discussed infra.

Intervention strategies to control the burden of chronic liver disease caused by HBV include primary prevention through vaccination and chemoprevention through antiviral therapy (Hoofnagle et al., 1993). Both of these strategies provide powerful selection pressures, which can result in the emergence of variant viruses or "escape" mutants. Such mutants may emerge as a function of four factors: the viral mutation frequency, the intrinsic mutability of the antiviral target site, the selective pressure and the magnitude and rate of virus replication (Richman, 1996).

Until recently, the only licensed treatment for chronic hepatitis B was interferon-alpha (IFN-α), which proves to be partially effective only in a small group of carriers (Lok, 1994). This relative failure of IFN-α for the treatment of chronic HBV infection has prompted the search for further therapeutic agents and regimes. In particular, a number of nucleoside analogues have been shown to inhibit hepadnaviral replication via inhibition of the hepadnaviral DNA polymerase/reverse transcriptase. Some of these compounds have already been withdrawn from clinical use due to toxicity (lobucavir) or lack of efficacy (famciclovir) (De Clercq, 1999; Schinazi, 1997; Luscombe et al., 1996). On the other hand, other compounds such as Adefovir Dipivoxil (Gilead Sciences) and Entecavir (Bristol Myers Squibb) show much promise and are currently in phase III clinical trials. At this moment, the most successful nucleoside analogue is without doubt lamivudine (Jarvis et al., 1999), which was recently licensed. Lamivudine is a deoxycytidine analogue, which is phosphorylated by histidine kinases to a triphosphate moiety that is active against HBV (Wang et al., 1998). Lamivudine inhibits HBV replication, reduces hepatic necroinflammatory activity and the progression of fibrosis in patients with chronic hepatitis B (Yao et al., 1999; Lai et al., 1998; Dienstag et al., 1998; Schiff et al., 1998). Lamivudine also reduces ongoing viral replication and compensated liver disease including HBe-Ag negative patients (Tassopoulos et al., 1999). The drug also suppresses viral replication in liver transplant recipients and HIV-positive patients (Markowitz et al., 1998; Wright et al., 1997; Benhamou et al., 1996). However, lamivudine-resistant DNA polymerase variants have been isolated from patients with chronic hepatitis B during treatment with lamivudine (Hunt et al., 2000; Nafa et al., 2000; Yeh at al., 2000; Ling et al., 1999) and references therein). One year of treatment with lamivudine (100 mg daily) results in the appearance of the 'YVDD' mutation (wild-type motif is 'YMDD') in the DNA polymerase in 14-43% of HBV-infected patients (Dienstag et al., 1999; Lai et al., 1998). The mutation rate increases with prolonged use of lamivudine (Liaw et al., 2000). Another lamivudine-induced mutation turns the YMDD motif into YIDD. Both mutations of the amino acid residue 552 (see, however, Table 1 for the HBV genotype-dependent numbering of the amino acid residues) in the C-domain of the HBV DNA polymerase/reverse transcriptase (i.e. M552V and M552I) can occur in combination with another mutation in the B-domain of the HBV DNA polymerase/reverse transcriptase, namely the L528M mutation. The M552V and M552I mutations alone, as well as combination of either one with the L528M mutation have been shown to confer resistance of HBV replication to lamivudine and famciclovir (Ono et al., 2001; Xiong et al., 2000; Delaney et al., 2000; Ono-Nita et al., 2000; Fu et al., 1999; Xiong et al., 1998). Another associated mutation is the V/L/M555I mutation which, either alone or in combination with M552I is conferring low resistance of HBV replication to lamivudine or famciclovir (Fu et al., 1999).

Both in vitro and in vivo studies have demonstrated that YMDD variants, i.e. HBV variants comprising 'YVDD' or 'YIDD' in the C-domain of the HBV DNA polymerase/reverse transcriptase are less replication competent compared to the wild-type, are associated with lower HBV DNA levels compared to pretreatment levels, and can be associated with continued histologic improvement (Leung, 2000; Ling et al., 1999; Ono-Nita et al., 1999). However, said YMDD variants have also been reported to cause hepatic decompensation (Liaw et al., 1999). As for the limited studies completed at this moment, lamivudine-resistant HBV does not confer cross-resistance to adefovir (Xiong et al., 1998).

At least some of the lamivudine-induced mutations appearing in the HBV DNA polymerase also occur after prolonged treatment with famciclovir and are described in e.g. Bartholomeusz et al. (1998) (International Patent Publication Number WO 98/21317) and Bartholomeusz et al. (2000) (International Patent Publication Number WO 00/61758). A comprehensive review of HBV resistance to antiviral drugs is given in (Delaney et al., 2001).

Key mutations involved in lamivudine-resistance of the HBV DNA polymerase/transcriptase have been identified as L180M, M204V/I and MN/L207I (see, however, Table 1 for HBV genotype-dependent numbering of amino acid 204 in the HBV DNA polymerase/reverse transcriptase).

It is known in the art that HIV (human immunodeficiency virus) also contains the YMDD motif in its reverse transcriptase domain. By means of in vitro mutagenesis, said motif of the HIV reverse transcriptase has been converted into YSDD. The resulting mutant HIV reverse transcriptase was only 5 to 10% as active in vitro as the wild-type HIV reverse transcriptase (Wakefield et al., 1992). In the same study, however, it is not at all mentioned that said mutation could be induced by treatment of a HIV-infected patient with an antiviral drug, i.e. could occur in vivo. Nor is it mentioned that the YMDD motif is part of the HBV DNA polymerase/reverse transcriptase. The occurrence of the YSDD mutation in the HBV DNA polymerase during lamivudine-treatment of a HBV-infected patient was described by Bozdayi et al. (Bozdayi et al., 2001).

SUMMARY OF THE INVENTION

The present invention relates to an isolated HBV polynucleic acid or a fragment thereof, said polynucleic acid or said fragment characterized in that it comprises codon 204 of the HBV reverse transcriptase domain wherein said codon 204 is encoding a serine. Said isolated HBV polynucleic acid or fragment can further be characterized in that it also comprises codon 180 of the HBV reverse transcriptase domain wherein said codon 180 is encoding a methionine. Furthermore, said HBV polynucleic acid or fragment thereof may be defined by SEQ ID NO:6 or the complement thereof, or said fragment may be derived from SEQ ID NO:6 or the complement thereof.

The invention further relates to an isolated HBV DNA polymerase/reverse transcriptase protein or a fragment thereof, said protein or fragment characterized in that it comprises amino acid 204 of the HBV reverse transcriptase domain and wherein said amino acid 204 is a serine. Said HBV DNA polymerase/reverse transcriptase protein or fragment thereof may be characterized further in that it also comprises amino acid 180 of the HBV reverse transcriptase domain and wherein said amino acid 180 is a methionine. Furthermore, the HBV DNA polymerase/reverse transcriptase protein or fragment thereof may be encoded by the isolated HBV polynucleic acid or fragment thereof according to the invention. An exemplary HBV DNA polymerase/reverse transcriptase protein or fragment thereof according to the invention is defined by SEQ ID NO:4. An exemplary HBV DNA polymerase/reverse transcriptase protein fragment according to the invention is derived from SEQ ID NO:4.

Said isolated HBV polynucleic acid sequence or fragment thereof, or the amino acid sequences derived thereof, may furthermore be in ASCII-, hexadecimal- or UNICODE code, in a single-byte, double-byte or multiple-byte character set or in a binary code. The invention further covers computer readable carriers and computer readable databases comprising said sequences in ASCII-, hexadecimal- or UNICODE code, in a single-, double- or multi-byte character set or in binary code.

The invention is also related to an isolated HBV variant comprising a polynucleic acid or fragment thereof according to the invention, more specifically a polynucleic acid or fragment thereof comprising a serine-encoding codon 204 or a methionine-encoding codon 180 and a serine-encoding codon 204 in the HBV reverse transcriptase domain. The isolated HBV variant alternatively comprises a protein or fragment thereof comprising a serine at position 204 or a methionine at position 180 and a serine at position 204 of the HBV reverse transcriptase domain.

The present invention also comprises a vector comprising the HBV polynucleic acid or fragment thereof according to the invention.

The present invention relates as well to a host cell comprising the MY polynucleic acid or fragment thereof according to the invention, the HBV DNA polymerase/reverse transcriptase protein or fragment thereof according to the invention, the HBV variant according to the invention, or the vector according to the invention.

Further included in the invention are methods and diagnostic kits for detecting the presence of a HBV virus in a biological sample; and/or for detecting resistance to an antiviral drug of a HBV virus present in a biological sample; and/or for detecting the presence of a serine-encoding codon 204 or a methionine-encoding codon 180 and a serine-encoding codon 204 of the HBV reverse transcriptase domain of a HBV virus present in a biological sample; and/or for detecting the presence of a valine-encoding codon 196 of the small HBV viral surface antigen open reading frame of a HBV virus present in a biological sample. More specifically are covered said methods and said diagnostic kits based on determining the nucleic acid sequence. Alternatively, said methods and said diagnostic kits are based on a hybridization assay.

Also embodied by the present invention are oligonucleotides capable of discriminating, in a HBV polynucleic acid or fragment thereof according to the invention, a codon 204 encoding a serine from a codon 204 encoding a methionine, valine or isoleucine in the HBV reverse transcriptase domain.

Furthermore contemplated in the invention are methods for screening for drugs active against a HBV virus comprising a polynucleic acid or fragments thereof according to the invention, or HBV DNA polymerase/reverse transcriptase or fragments thereof according to the invention. Said method may comprise measuring replication of said HBV virus or measuring a DNA polymerase/reverse transcriptase activity of said HBV virus. More specifically, said methods further comprise obtaining said HBV virus from a biological sample.

The current invention further relates to isolated HBV variants, isolated HBV DNA polymerase/reverse transcriptase, or isolated HBV viral surface antigens, or parts thereof, comprising a novel mutation or comprising a combination of mutations. Said mutations comprise the M204S or the L180M and M204S mutations in the HBV reverse transcriptase domain. Said mutations further comprise the W196V mutation in the HBV small viral surface antigen open reading frame.

The invention is also covering the use of a method of the invention or a diagnostic kit of the invention to follow progression of HBV, and possibly HDV, infection. Other uses of said methods of the invention or diagnostic kits of the invention include monitoring the occurrence of resistance to an antiviral drug and adaptation of a therapeutic regimen against HBV, and possibly HDV, infection due to the occurrence of resistance to an antiviral drug.

FIGURE AND TABLE LEGENDS

FIG. 1. Schematic Representation of Patient History.

The X-axis represents the time line. Underneath the X-axis the different treatments of HBV-infected patient No. 7 are indicated (5 MIU Intron A=5 million units of interferon three times a week; LAM=lamivudine). On the left Y-axis, the ALT-levels (alanine amino-transferase; in IU/L, International Units/L) are given. ALT-levels in serum samples of patient No. 7 are indicated by the bars. On the right Y-axis, the viral DNA load (in pg HBV DNA/mL serum as determined using the liquid hybridization assay of Digene, US) are given. The HBV DNA levels in serum samples of patient No. 7 are indicated by the solid line linking the diamonds. The vertical arrow at the top of the figure indicates the ALT-flare coinciding with the onset of viral breakthrough.

FIG. 2. Alignment of HBV DNA Polymerase Protein Sequences.

Aligned are a HBV genotype D fragment of the HBV DNA polymerase/reverse transcriptase amino acid sequence derived from Genbank accession number X02496 ("HBVD RT"; the derived amino acid sequence is defined by SEQ ID NO:1) and the corresponding amino acid sequence derived from the HBV DNA isolated from patient No. 7 ("P7RT"; defined by SEQ ID NO:4). Amino acids in P7RT identical to the HBVD RT sequence are indicated with a '●'. Amino acids differing between both sequences are indicated in a black shaded box. Numbering of the amino acid residues in the reverse transcriptase domain ("RT") of the HBV DNA polymerase/reverse transcriptase are indicated above the alignment and are compliant with the universal numbering system proposed by Stuyver et al. (2001).

FIG. 3. Alignment of HBV HBsAg Protein Sequences.

Aligned are a HBV genotype D fragment of the HBsAg amino acid sequence derived from Genbank accession number X02496 ("HBVD S"; the derived amino acid sequence is defined by SEQ ID NO:2) and the corresponding amino acid sequence derived from the HBV DNA isolated from patient No. 7 ("P7S"; defined by SEQ ID NO: 5). Amino acids in P7S identical to the HBVD S sequence are indicated with a '●'. Amino acids differing between both sequences are indicated in a black shaded box. Numbering of the amino acid residues in the HBV HBsAg are indicated above the alignment and are compliant with the universal numbering system proposed by Stuyver et al. (2001).

FIG. 4. Alignment of HBV DNA Nucleotide Sequences.

Aligned are a HBV genotype D nucleotide sequence as given by Genbank accession number X02496 ("HBVD"; defined by SEQ ID NO:3) and the corresponding nucleotide sequence of the HBV DNA isolated from patient No. 7 ("P7"; defined by SEQ ID NO:6). Nucleotides in P7 identical to the HBVD sequence are indicated with a '●'. Nucleotides differing between both sequences are indicated in a black shaded box. Numbering of the nucleotides in the reverse transcriptase domain ("RT") of the HBV DNA polymerase/reverse transcriptase are indicated next to the alignment and are according to the nucleotide-numbering of the DNA sequence given in Genbank accession number X02496. The DNA region of HBVD encoding the YMDD motif is underlined.

TABLE 1

Genotype-dependent numbering and consensus number of methionine residue in YMDD-motif of the HBV DNA polymerase (Stuyver et al., 2001) and indication of the mutation in the YMDD motif as present in the HBV strain isolated from lamivudine-treated HBV-infected patient No. 7.

| | |
|---|---|
| Position (HBV genotype A) | 552 |
| Position (HBV genotypes B, C, F) | 550 |
| Position (HBV genotype D) | 539 |
| Position (HBV genotypes E, G) | 549 |
| Position (HBV consensus RT domain) | 204 |
| Wild-type amino acid residue | M |
| Mutation in HBV strain from patient No. 7 | S |

As exemplified above, the consensus numbering of codons of Stuyver is independent from the HBV genotype. By this method, numbering the polymerase of HBV starts with the highly conserved EDWGPCDEHG motif making the total length of the HBV reverse transcriptase/polymerase (rt domain) 344 amino acids long and genotype independent (see page 753, second column of Stuyver et al. ("Nomenclature for Antiviral-Resistant Human Hepatitis B Virus Mutations in the Polymerase Region" Hepatology 2001:33; 751-757).

TABLE 2

Characters relevant to amino acid and nucleic acid sequences with their ASCII code, hexadecimal (HEX) code and binary code (ASCII: 7 most right digits; UNICODE: all 16 digits). HEX code = UNICODE for the listed characters.

| Character | ASCII code | HEX code | Binary code |
|---|---|---|---|
| A | 65 | 0041 | 000000000 1000001 |
| B | 66 | 0042 | 000000000 1000010 |
| C | 67 | 0043 | 000000000 1000011 |
| D | 68 | 0044 | 000000000 1000100 |
| E | 69 | 0045 | 000000000 1000101 |
| F | 70 | 0046 | 000000000 1000110 |
| G | 71 | 0047 | 000000000 1000111 |
| H | 72 | 0048 | 000000000 1001000 |
| I | 73 | 0049 | 000000000 1001001 |
| K | 75 | 004B | 000000000 1001011 |
| L | 76 | 004C | 000000000 1001100 |
| M | 77 | 004D | 000000000 1001101 |
| N | 78 | 004E | 000000000 1001110 |
| P | 80 | 0050 | 000000000 1010000 |
| Q | 81 | 0051 | 000000000 1010001 |
| R | 82 | 0052 | 000000000 1010010 |
| S | 83 | 0053 | 000000000 1010011 |
| T | 84 | 0054 | 000000000 1010100 |
| V | 86 | 0056 | 000000000 1010110 |
| W | 87 | 0057 | 000000000 1010111 |
| X | 88 | 0058 | 000000000 1011000 |
| Y | 89 | 0059 | 000000000 1011001 |
| a | 97 | 0061 | 000000000 1100001 |
| b | 98 | 0062 | 000000000 1100010 |
| c | 99 | 0063 | 000000000 1100011 |

TABLE 2-continued

Characters relevant to amino acid and nucleic acid sequences with their ASCII code, hexadecimal (HEX) code and binary code (ASCII: 7 most right digits; UNICODE: all 16 digits). HEX code = UNICODE for the listed characters.

| Character | ASCII code | HEX code | Binary code |
|---|---|---|---|
| d | 100 | 0064 | 000000000 1100100 |
| e | 101 | 0065 | 000000000 1100101 |
| f | 102 | 0066 | 000000000 1100110 |
| g | 103 | 0067 | 000000000 1100111 |
| h | 104 | 0068 | 000000000 1101000 |
| i | 105 | 0069 | 000000000 1101001 |
| k | 107 | 006B | 000000000 1101011 |
| l | 108 | 006C | 000000000 1101100 |
| m | 109 | 006D | 000000000 1101101 |
| n | 110 | 006E | 000000000 1101110 |
| p | 112 | 0070 | 000000000 1110000 |
| q | 113 | 0071 | 000000000 1110001 |
| r | 114 | 0072 | 000000000 1110010 |
| s | 115 | 0073 | 000000000 1110011 |
| t | 116 | 0074 | 000000000 1110100 |
| v | 118 | 0076 | 000000000 1110110 |
| w | 119 | 0077 | 000000000 1110111 |
| x | 120 | 0078 | 000000000 1111000 |
| y | 121 | 0079 | 000000000 1111001 |

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

During work leading to the present invention, it became clear that a previously unrecognized lamivudine-induced mutation existed in HBV. Sequence analysis of isolated HBV DNA confirmed this finding and revealed the emergence of a novel nucleic acid polymorphism at codon 204 of the HBV reverse transcriptase domain. Said polymorphism results in the mutation M204S in the HBV DNA polymerase/reverse transcriptase, thus converting the "YMDD" motif into "YSDD". The occurrence of said polymorphism furthermore coincided with viral breakthrough, a strong indication for the emergence of a lamivudine-resistant HBV variant. In order to assess the presence of a HBV virus in a biological sample as well as to assess the presence of drug-resistant HBV mutants in a biological sample, an assay which enables the detection of mutations causing drug-resistance is necessary. The newly identified polymorphism thus poses an additional technical problem of developing an assay enabling detection of HBV viruses carrying said novel polymorphism.

The solution to the technical problems is achieved by providing the embodiments characterized in the claims.

A first aspect of the present invention relates to an isolated HBV polynucleic acid or a fragment thereof, said polynucleic acid or said fragment characterized in that it comprises codon 204 of the HBV reverse transcriptase domain wherein said codon 204 is encoding a serine. Alternatively, said isolated HBV polynucleic acid or fragment is further characterized in that it also comprises codon 180 of the HBV reverse transcriptase domain wherein said codon 180 is encoding a methionine. In a specific embodiment, said HBV polynucleic acid or fragment thereof is defined by SEQ ID NO:6 or the complement thereof, or said fragment may be derived from SEQ ID NO:6 or the complement thereof.

In a further embodiment, said isolated HBV polynucleic acid or fragment thereof according may be DNA, or RNA wherein T is replaced by U, or which is a synthetic polynucleic acid.

Another aspect of the current invention relates to an isolated EBV DNA polymerase/reverse transcriptase protein or a fragment thereof, said protein or fragment characterized in that it comprises amino acid 204 of the HBV reverse transcriptase domain and wherein said amino acid 204 is a serine. In a specific embodiment, said HBV DNA polymerase/reverse transcriptase protein or fragment thereof is characterized further in that it comprises amino acid 180 of the HBV reverse transcriptase domain and wherein said amino acid 180 is a methionine. Said HBV DNA polymerase/reverse transcriptase protein or fragment thereof is, in another embodiment, encoded by the isolated HBV polynucleic acid or fragment thereof according to the invention. More specifically, said HBV DNA polymerase/reverse transcriptase protein or fragment thereof is defined by SEQ ID NO:4, or said fragment is derived from SEQ ID NO:4.

The isolated polynucleic acid or fragment thereof according to the invention is meant to comprise single-stranded polynucleic acids, double-stranded polynucleic acids or triplex-forming polynucleic acids obtained directly from a sample or obtained after duplication, multiplication or amplification. "Obtained" is, in the present context, meant to include isolation and/or purification and/or amplification of said polynucleic acids from a biological sample. The "sample" may be any biological material taken either directly from an infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc. Biological material may also be artificially infected cell cultures or the liquid phase thereof. "Duplication, multiplication or amplification" is meant to include any nucleic acid produced by using any nucleic acid amplification method including any sequencing technique. Thus, any sequencing technique producing a nucleic acid molecule comprising any of said, or a combination of said nucleic acid polymorphisms is to be understood to be comprised in the term "duplication, multiplication or amplification".

The term "synthetic polynucleic acid" as referred to herein is meant to be a single-stranded polynucleic acid, double-stranded polynucleic acid or triplex-forming polynucleic acid. Polynucleic acids can be made in vitro by means of a nucleotide sequence amplification method. If such an amplified polynucleic acid is double-stranded, conversion to a single-stranded molecule can be achieved by a suitable exonuclease given that the desired single-stranded polynucleic acid is protected against said exonuclease activity. Alternatively, polynucleic acid are derived from recombinant plasmids containing inserts including the corresponding polynucleotide sequences, if need be by cleaving the latter out from the cloned plasmids upon using the adequate nucleases and recovering them, e.g. by fractionation according to molecular weight. Another means of making a synthetic polynucleic acid in vitro is comprised within any method of nucleic acid sequencing. Products of a sequencing reaction are thus clearly covered by the term "synthetic polynucleic acid". The polynucleic acids according to the present invention can also be synthesized chemically, for instance by applying the conventional phospho-triester or phosphoramidite chemistry.

"Nucleotide sequence (DNA or RNA) amplification" is meant to include all methods resulting in multiplication of the number of target nucleotide sequence copies. Nucleotide sequence amplification methods include the polymerase chain reaction (PCR; DNA amplification), strand displacement amplification (SDA; DNA amplification), transcription-based amplification system (TAS; RNA amplification), self-sustained sequence replication (3SR; RNA amplification), nucleic acid sequence-based amplification (NASBA; RNA amplification), transcription-mediated amplification (TMA; RNA amplification), Qbeta-replicase-mediated amplification and run-off transcription.

The most widely spread nucleotide sequence amplification technique is PCR. Basically, two primers, a sense and an antisense are annealed to a denatured DNA substrate and extended by a thermostable DNA polymerase. The latter allows rapid and repeated thermal cycling (denaturing/annealing/extension in three-step PCR; denaturing/annealing+ extension in two-step PCR). The target DNA is exponentially amplified. Many methods rely on PCR including AFLP (amplified fragment length polymorphism), IRS-PCR (interspersed repetitive sequence PCR), iPCR (inverse PCR), RAPD (rapid amplification of polymorphic DNA), RT-PCR (reverse transcription PCR) and real-time PCR. Some of the latter methods are explained in more detail infra. RT-PCR can be performed with a single thermostable enzyme having both reverse transcriptase and DNA polymerase activity (Myers et al., 1991). Alternatively, a single tube-reaction with two enzymes (reverse transcriptase and thermostable DNA polymerase) is possible (Cusi et al., 1994).

SDA is, contrary to PCR, an isothermal DNA replication method. Sense and antisense primers used in this method have a 5'-terminal overhang comprising a restriction enzyme recognition site. Both primers are extended by the Klenow polymerase in the presence of an alpha-S-dNTP. The resulting hemiphosphorothiolated dsDNA is subsequently nicked in the unmodified strand (ss-nick) by the restriction enzyme. This enables the Klenow polymerase to extend the resulting primer fragments thereby displacing the downstream non-template strand (Walker et al., 1992).

In TAS, a first sense primer comprising at its 5' end a promoter recognized by a DNA-dependent RNA polymerase (such as bacteriophage T7, T3 or SP6 RNA polymerase) and a second antisense primer complementary to the 3' end of the RNA to be amplified are used to prime reverse transcription. After denaturation and reannealing of the primers another round of reverse transcription can take place and the ssDNA strands formed in the first RT reaction either used as a substrate for RT or anneal, in both cases forming a dsDNA comprising the intact DNA-dependent RNA polymerase promoter. Formation of said intact promoter allows transcription and synthesis of multiple copies of the original target RNA (Kwoh et al., 1989). 3SR is based on a similar principle as TAS but both primers now carry the same DNA-dependent RNA polymerase promoter. Furthermore, after RT, the RNA/DNA hybrid is converted into ssDNA by means of RNAseH. Denaturation is thus not longer required which also alleviates the need to add fresh reverse transcriptase enzyme after each round of denaturation. 3SR thus is an isothermal variant of TAS (Gingeras et al., 1990).

NASBA is a hybrid between TAS and 3SR using a single primer including the DNA-dependent RNA polymerase promoter and using RNAseH (Kievits et al., 1991).

TMA is similar to NASBA but has ribosomal RNA as template. Detection of the amplified rRNA sequences is achieved by chemiluminescence detection of amplicons with an acridium ester-labeled DNA probe in the hybridization protection assay (HPA) (Stary et al., 1998). Qbeta-replicase-mediated amplification is based on the capability of the RNA-directed RNA is polymerase of phage Qbeta to isothermally amplify RNA in vitro. RNAs heterologous to the Qbeta phage can be amplified by coupling them to cognate RQ RNAs (Lizardi et al., 1988).

Run-off transcription is a method commonly used in e.g. the preparation of riboprobes or RNA probes. The DNA of interest is placed behind the promoter recognized by a DNA-dependent RNA polymerase (e.g. T3, T7, SP6 RNA polymerase), e.g. by cloning in a suitable vector. The DNA of interest is furthermore digested with a restriction enzyme at a suitable site such that the desired riboprobe can be synthesized by the RNA polymerase. When said RNA polymerase reaches the digested end of the DNA, it runs off the substrate and is available for a new round of RNA synthesis. Run-off transcription is also applicable to amplify any given target (poly)nucleic acid operably linked to a suitable DNA-dependent RNA polymerase promoter.

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with nonamplifiable monomers such as HEG (hexethylene glycol).

Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

Modifications of nucleotides include the addition of acridine or derivatives thereof, ACRYDITE, amine, biotin, BHQ-1, BHQ-2, BHQ-3, borane dNTPs, carbon spacers (e.g. $C_3$, $C_6$, $C_7$, $C_9$, $C_{12}$ or $C_{18}$), cascade blue, cholesterol, coumarin or derivatives thereof, Cy3, Cy3.5, Cy5, Cy5.5, Cy7 DABCYL, dansylchloride, digoxigenin, dinitrophenyl, dual biotin, EDANS, 6-FAM, fluorescein, 3'-glyceryl, HEX, IAEDANS, inverted dA, inverted dG, inverted dC, inverted dG, IRD-700, IRD-800, JOE, La Jolla Blue, metal clusters such as gold nanoparticles, phenylboronic acid, phosphate psoralen, 3'- or 5'-phosphorylation, pyrene, 3' ribo-adenosine, 3' ribo-guanosine, 3' ribo-cytidine, (LC) Red640, (LC) Red705, rhodamine, ROX, thiol (SH), spacers, TAMRA, TET, AMCA-S, SE, BODIPY, MARINA BLUE, OREGON GREEN, PACIFIC BLUE, QSY7, RHODAMINE GREEN, RHODAMINE RED, RHODOL GREEN, tetramethyl-rhodamine, TEXAS RED, Uni-Link $NH_2$-modifier, radiolabels (e.g. $^{125}I$, $^{131}I$, $^{35}S$, $^{14}C$, $^{32}P$, $^{33}P$, $^3H$) and nanoparticles.

Polynucleotide backbone and base modifications further include 2'-deoxyaristeromecyin, methylphosphonate, 2'-OMe-methylphosphonate RNA, 2'-O-(2-methoxyethyl), phosphorothioate, alkylphosphorothiate, phosphoramidite, RNA, 2'-OMeRNA, 2-amino-dA, 2-aminopurine, 3'-(ddA), 3' dA (cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU.

Further modifications of polynucleotides include hapten- or protein-labeling. Haptens include e.g. biotin and digoxigenin whereas proteins include enzymes such as soybean or horseradish peroxidase, beta-galactosidase, luciferase, alkaline phosphatase, glutathione S-transferase or dihydrofolate reductase or may constitute heterologous epitopes such as (histidine)$_6$-tag, protein A, maltose-binding protein, Tag●100 epitope (EETARFQPGYRS; SEQ ID NO:11), c-myc epitope (EQKLISEEDL; SEQ ID NO:12), FLAG®-epitope (DYKDDDK; SEQ ID NO:13), lacZ, CMP (calmodulin-binding peptide), HA epitope (YPYDVPDYA; SEQ ID NO:14), protein C epitope (EDQVDPRLIDGK; SEQ ID NO:15) and VSV epitope (YTDIEMNRLGK; SEQ ID NO:16). Other proteins include histones, single-strand binding protein (ssB) and native and engineered fluorescent proteins such as green-, red-, blue-, yellow-, cyan-fluorescent proteins. Crosslinking moieties can also be incorporated such as coumarins, furocoumarins or benzodipyrones, or derivates of any thereof.

Said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optimally from 12 to 18 bases in length (Nielsen, 2001). Said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells. (Orum et al., 2001; Wahlestedt et al., 2000). In general, chimeras or mix-mers of any of DNA, RNA, PNA and LNA are considered as well as any of these wherein thymine is replaced by uracil.

The term "nucleic acid polymorphism" or "nucleotide sequence polymorphism" is meant to include any difference in the primary nucleotide sequence of the nucleic acid under investigation relative to the primary nucleotide sequence of one or more reference nucleic acids. The most simple nucleic acid polymorphism is a polymorphism affecting a single nucleotide, i.e. a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The above explanation also clarifies terms like "polymorphic variant".

In yet another embodiment, said isolated HBV polynucleic acid sequences or fragments thereof, or the amino acid sequences derived thereof, may be in ASCII-, hexadecimal- or UNICODE code, in a single-byte, double-byte or multiple-byte character set or in a binary code. In an additional embodiment, said sequences in ASCII-, hexadecimal- or UNICODE code, in a single-, double- or multi-byte character set or in binary code are readable by a computer. In a further embodiment, said sequences in in ASCII-, hexadecimal- or UNICODE code, in a single-, double- or multi-byte character set or in binary code are recordable on a computer readable carrier or are incorporatable in a computer-readable database. In yet another embodiment is covered computer readable carriers comprising said sequences in ASCII-, hexadecimal- or UNICODE code, in a single-, double- or multi-byte character set or in binary code. In yet another further embodiment of the invention is envisaged a computer readable database comprising said sequences in ASCII-, hexadecimal- or UNICODE code, in a single-, double- or multi-byte character set or in binary code. In yet another further embodiment, said sequences in ASCII-, hexadecimal- or UNICODE code, in a single-, double- or multi-byte character set or in binary code are used in algorithms capable of comparing sequences or capable of aligning sequences.

"Computer readable carriers" or "computer readable media" include all carriers and media accessible and readable with a computer. Said carriers and media include magnetic tapes, floppy disks, hard disks, ZIP disks, CD-ROMs, electrical or electronical memories such as RAM and ROM and hybrid magnetic/optical storage media. Data on a carrier or a medium are recorded as a binary code. Any software run on a computer forms an interface transforming the binary code into a sequence information format readable by man (e.g. as a text or formatted text on e.g. a screen, a monitor or printed on a sheet of paper, on a slide, on textile etc.) or vice versa. Entering in a computer (e.g. via the keyboard) a sequence in said format readable by man thus has the technical effect of transformation by said computer (combination of hardware and software) of said sequence into a unique binary code. Said unique binary code can be recorded on a computer readable carrier or medium, or, alternatively be displayed on e.g. a screen or a monitor or be printed. Vice versa, reading of a unique binary code associated with a given sequence by a computer (combination of hardware and software) has the technical effect of transformation by said computer of said code into a sequence information format readable by man.

Different codes for interchange of information have been designed. The ASCII (American Standard Code for Information Interchange) is a universal standard (7-bits per byte code) for the representation of characters in computer devices. For instance, the ASCII number 65 is representing the character 'A' (capital A) and is linked to the binary code '1000001' whereby said binary code is read from right to left. In the hexadecimal code, the character 'A' (capital A) is assigned the HEX number 0041. The EBCDIC (Extended Binary-Coded Decimal Interchange Code) encoding format was designed by IBM and is an 8-bits per byte code. ASCII is a single-byte character sets (SBCS). Another SBCS is ISO-8859-1, an 8-bit superset of ASCII; a modernized version thereof is ISO-885945. In double-byte character sets (DBCS), a single character is represented by two bytes. Multi-byte character sets (MBCS) use a variable number of bytes per character. MBCSs are often compatible with ASCII; i.e. the Latin letters are represented in such encodings with the same bytes that ASCII uses. A more recent code is UNICODE which is currently representing over 65000 characters whereas the ASCII and EBCDIC codes are limited to 256 characters. UNICODE UTF-16 is the current standard and uses one or two 16-bit code units for each code point. UNICODE designates a unique number to each character independent of platform, program or programming language. As an example, the UNI- CODE for 'A' (capital A) is 65-[ASCII] (i.e. the same number as in ASCII) or 0041-[HEX] (i.e. the same number as in the hexadecimal code) and is linked to the binary code '0000000001000001', i.e. the same binary code as in the ASCII system but extended to the left with 9 additional bits which all are '0' (zero). More information about UNICODE can be found at http://www.unicode.org. An overview of the ASCII and HEX codes and the corresponding binary codes in ASCII and UNICODE are given in Table 2. Table 2 comprises said codes for the indicated unformatted characters.

Another aspect of the invention is related to an isolated HBV variant comprising a polynucleic acid or fragment thereof according to the invention, more specifically a polynucleic acid or fragment thereof comprising a serine-encoding codon 204 or a methionine-encoding codon 180 and a serine-encoding codon 204 in the HBV reverse transcriptase domain. The isolated HBV variant alternatively comprises a protein or fragment thereof comprising a serine at position 204 or a methionine at position 180 and a serine at position 204 of the HBV reverse transcriptase domain.

In a further aspect of the present invention is comprised a vector comprising the isolated HBV polynucleic acid or fragment thereof according to the invention. In a specific embodiment, said vector is an expression vector. In another specific embodiment, said vector is a viral vector.

In a further embodiment, said vector is a universal cloning vector such as the pUC-series or pEMBL-series vectors or cloning vectors such as cloning vectors requiring a DNA topoisomerase reaction for cloning, TA-cloning vectors and recombination-based cloning vectors such as those used in the Gateway system (InVitrogen). Vectors comprise plasmids, phagemids, cosmids, bacmids (baculovirus vectors) or may be viral or retroviral vectors. A vector can merely function as a cloning tool and/or -vehicle or may additionally comprise regulatory sequences such as promoters, enhancers and terminators or polyadenylation signals. Said regulatory sequences may enable expression of the information contained within the DNA fragment of interest cloned into a vector comprising said regulatory sequences. Expression may be the production of RNA molecules or mRNA molecules and, optionally, the production of protein molecules thereof. Expression may be the production of an RNA molecule by means of a viral polymerase promoter (e.g. SP6, T7 or T3 promoter) introduced to the 5'- or 3'-end of the DNA of interest. Expression may furthermore be transient expression or stable expression or, alternatively, controllable expression. Controllable expression comprises inducible expression, e.g. using a tetracyclin-regulatable promoter, a stress-inducible (e.g. human hsp70 gene promoter), a methallothionine promoter, a glucocorticoid promoter or a progesterone promoter. Promoters further include HBV promoters such as the core promoter and heterologous promoters such as the cytomegalovirus (CMV) immediate early (IE) promoter. A promoter can also preferably drive expression in liver tumour cells, e.g. the promoter and enhancer of the alpha-foetoprotein gene. Expression vectors are known in the art that mediate expression in bacteria (e.g. *Escherichia coli, Streptomyces* species), fungi (e.g. *Saccharomyces cerevisiae, Schizosaccharomyces pombe, Pichia pastoris, Aspergillus* species, *Hansenula polymorpha, Neurospora crassa*), insect cells (*Spodoptera frugiperda* cells, Sf9 cells), plant cells (e.g. potato virus X-based expression vectors, see e.g. Vance et al. 1998 in International Patent Publication No. WO98/44097) and mammalian cells (e.g. CHO or COS cells, Vero cells, cells from the HeLa cell line). Particularly suited host cells in the context of the present invention are mammalian, e.g. human, primary hepatocytes, hepatoma cell lines (e.g. HepG2, HepT1, HepT3, Huh6, Huh7), Chang liver cells, rodent liver cells, primate liver cells, hominoid liver cells, or any other mammalian, e.g. human, host cells or cell line. A vector, or an expression vector, may furthermore be capable of autonomous replication in a host cell or may be an integrative vector, i.e. a vector completely or partially, and stably, integrating in the genome of a host cell. Integration of any first DNA fragment, e.g. a vector or a fragment thereof; in any other second DNA fragment, e.g. the genome of a host cell, can be reversed if said first DNA fragment is flanked e.g. by site-specific recombination sites or by repeat sequences typical for transposons. Alternatively, said site-specific recombination sites or transposon-repeat sequences are comprised in said second DNA fragment and are flanking said first DNA fragment. In yet another alternative, said first DNA fragment can possibly be introduced in a thereto suitable second DNA fragment by homologous recombination and the same process can be used to exchange said first DNA fragment with another thereto suitable DNA fragment.

Introduction of a vector, or an expression vector, into a host cell may be effectuated by any available transformation or transfection technique applicable to said host cell as known in the art. Such transformation or transfection techniques comprise heat-shock mediated transformation (e.g. of *E. coli*), conjugative DNA transfer, electroporation, PEG-mediated DNA uptake, liposome-mediated DNA uptake, lipofection, calcium-phosphate DNA coprecipitation, DEAE-dextran mediated transfection, direct introduction by e.g. microinjection or particle bombardment, or introduction by means of a virus, virion or viral particle.

Infection of e.g. HepG2 cell cultures by HBV viruses (e.g. derived from a patient's serum or from a cell culture) is normally not occurring but may be stimulated by pretreatment of the host cells with dimethylsulfoxide (DMSO; (Paran et al., 2001)). Alternatively, digestion of HBV with V8 protease results in infectious HBV viruses (Lu et al., 1996). A similar protease modification of at least one other hepadnavirus, woodchuck hepatitis virus (WHV), likewise results in WHV viruses which are infectious for human hepatoblastoma cells (Lu et al., 2001). Expression of HBV genes in hepatoblastoma cells was reported to increase significantly by lowering the incubation temperature from 37° C. to 32° C. (Kosovsky et al., 2000).

Vectors suited for assaying viral replication efficiency, more particularly for assaying HBV replication efficiency, include viral vectors or vectors comprising at least 1 unit (full-length) HBV genome, preferably greater than 1 unit HBV genome, e.g. 1.1, 1.2, 1.28, 1.3, 1.4, 1.5, 1.6, 1.7, 1.8, 1.9, 2.0, 3.0 or 4.0 times the HBV genome. One example of a viral vector system enabling HBV viral replication is a baculoviral system, e.g. as described by Isom and Harriet in International Patent Publication No WO99/37821 or by Delaney et al. (Delaney et al., 1999). The extent of viral replication can be monitored by measuring or detecting either one or more of (i) secrection of a HBV antigen (HBsAg or HBeAg), (ii) expression of HBV transcripts (3.5 kb-, 2.4 kb-, 2.1 kb-, 0.7 kb-transcripts), (iii) the amount of HBV replicative intermediates (relaxed circular DNA, double stranded DNA or single stranded DNA), (iv) the amount of HBV supercoiled circular (ccc) DNA, (v) the amount of secreted extracellular HBV DNA, (vi) the amount of extracellularly produced HBV particles, (vii) the amount of produced HBcAg protein, (viii) the amount of produced HBV DNA polymerase/reverse transcriptase protein, and (ix) the amount of produced HBV X protein. Another example of a viral vector system enabling HBV viral replication is a vector system which includes an indicator gene (e.g. a selectable marker gene or a screenable marker gene; e.g. as described by Capon and Petropoulos in U.S. Pat. No. 6,242,187), the expression of which is indicative for the extent of viral replication.

Viral vector systems enabling HBV viral replication are suited to compare replication efficiency of wild-type HBV viruses with replication efficiency of mutant HBV viruses. Mutant HBV viruses are understood to be HBV viruses comprising a mutation or a polynucleic acid polymorphism in either one or more of the HBV ORFs and/or the HBV regulatory sequences (e.g. promoter, enhancer, terminator or polyadenylation signal, epsilon-loop, encapsidation signal, repeat sequence, packaging signal, internal ribosome entry site).

A further aspect of the invention relates to a host cell comprising a HBV polynucleic acid or fragment thereof according to the invention, a HBV DNA polymerase/reverse transcriptase protein or fragment thereof according to the invention, a HBV variant according to the invention, or a vector according to the invention. In a specific embodiment, said host cell is a mammalian liver cell or a mammalian hepatoma cell.

The present invention further embraces the aspect of oligonucleotides capable of discriminating, in a HBV polynucleic acid or fragment thereof according to the invention, a serine-encoding codon 204 in the HBV reverse transcriptase domain from a codon 204 encoding a methionine, valine or isoleucine in the HBV reverse transcriptase domain.

The term "oligonucleotide" as referred to herein is meant to be a primer or a probe and may be single-stranded or double-stranded or may be part of a triplex-forming polynucleic acid. Oligonucleotides can be made in vitro by means of a nucleotide sequence amplification method. If such an amplified oligonucleotide is double-stranded, conversion to a single-stranded molecule can be achieved by a suitable exonuclease given that the desired single-stranded oligonucleotide is protected against said exonuclease activity. Alternatively, oligonucleotides are derived from recombinant plasmids containing inserts including the corresponding nucleotide sequences, if need be by cleaving the latter out from the cloned plasmids upon using the adequate nucleases and recovering them, e.g. by fractionation according to molecular weight. The oligonucleotides according to the present invention can also be synthetic, i.e. be synthesized chemically, for instance by applying the conventional phospho-triester or phosphoramidite chemistry. Oligonucleotides can further be synthesized in situ on a glass slide via solid-phase oligonucleotide synthesis or via photolitographic synthesis (Beaucage, 2001).

In another specific embodiment, the oligonucleotide according to the present invention further comprise a modification for attaching said oligonucleotide to a solid support. Said modification may for instance be an amine-, thiol-, 3-'propanolamine or Acrydite-modification of the oligonucleotide or may comprise the addition of a homopolymeric tail (e.g. an oligo(dT)-tail added enzymatically via a terminal transferase enzyme or added synthetically) to the oligonucleotide. If said homopolymeric tail is positioned at the 3'-terminus of the oligonucleotide or if any other 3'-terminal modification preventing enzymatic extension is incorporated in the oligonucleotide, the priming capacity of the oligonucleotide can be decreased or abolished. Other modifications are described in e.g. (Beaucage, 2001).

Clearly, oligonucleotides according to the present invention which are DNA, RNA, PNA or LNA, or which are any chimaera thereof are embodied in the invention. Further embodied are compositions comprising at least one oligonucleotide according to the invention.

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin or type of beads. Tools in molecular biology relying on such a process include the isolation of poly ($A^+$) mRNA. The hybridization process can furthermore occur with one of the complementary nucleic acids immobilized to a solid support such as a nitrocellulose or nylon membrane, a glass slide or fused silica (quartz) slide (the latter known as nucleic acid arrays or microarrays or as nucleic acid chips), a gold film, a polypyrrole film, an optical fiber or in e.g. a polyacrylamide gel or a microplate well. Tools in molecular biology relying on such a process include RNA and DNA gel blot analysis, colony hybridization, plaque hybridization, reverse hybridization and microarray hybridization. In order to allow hybridization to occur, the nucleic acid molecules are generally thermally, chemically (e.g. by NaOH) or electrochemically denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and $Na_3$-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (Sambrook et al., 1989) but the skilled craftsman will appreciate that numerous different hybridization conditions can be designed in function of the known or the expected homology and/or length of the nucleic acid sequence. Generally, for hybridizations with DNA probes without formamide, a temperature of 68° C., and for hybridization with formamide, 50% (v/v), a temperature of 42° C. is recommended. For hybridizations with oligonucleotides, the optimal conditions (formamide concentration and/or temperature) depend on the length and base composition of the probe and must be determined individually. In general, optimal hybridization for oligonucleotides of about 10 to 50 bases in length occurs approximately 5° C. below the melting temperature for a given duplex. Incubation at temperatures below the optimum may allow mismatched sequences to hybridize and can therefor result in reduced specificity. When using RNA oligonucleotides with formamide (50% v/v) it is recommend to use a hybridization temperature of 68° C. for detection of target RNA and of 50° C. for detection of target DNA. Alternatively, a high SDS hybridization solution can be utilized (Church et al., 1984). The specificity of hybridization can furthermore be ensured through the presence of a crosslinking moiety on the nucleic acid probe (e.g. Huan et al. 2000—WO00/14281). Said crosslinking moiety enables covalent linking of the nucleic acid probe with the target nucleotide sequence and hence allows stringent washing conditions. Such a crosslinking nucleic acid probe can furthermore comprise another label suitable for detection/quantification of the probe hybridized to the target.

The nucleic acid sequences of the invention may furthermore be linked to an external guide sequence (EGS) or a short external guide sequence (SEGS). Said guide sequences linked to a target sequence provide a minimal structure that is recognized as a substrate by RNAse P enzymes (Werner and George in U.S. Pat. No. 5,877,162). Nucleic acid sequences of the invention linked to an EGS or a SEGS may find therapeutic applications in treating HBV-infected patients.

Further aspects of the present invention are methods for detecting the presence of a HBV virus in a biological sample; and/or for detecting resistance to an antiviral drug of a HBV virus present in a biological sample; and/or for detecting the presence of a serine-encoding codon 204 or of a methionine-encoding codon 180 and a serine-encoding codon 204 in the HBV reverse transcriptase domain a HBV virus present in a biological sample; and/or for detecting the presence of a valine-encoding codon 196 in the small HBV viral surface antigen open reading frame of a HBV virus present in a biological sample.

With "codons 180 or 204 of or in the HBV reverse transcriptase domain" is meant the codons with consensus numbers 180 or 204, respectively, of the reverse transcriptase domain of the HBV DNA polymerase/reverse transcriptase open reading frame. Herein, said reverse transcriptase domain and consensus numbers are as defined by Stuyver et al. (Stuyver et al., 2001). Likewise, with "codon 196 of or in the small HBV viral surface antigen open reading frame" is meant the codon with consensus number 196 of the small HBV viral surface antigen open reading frame. Herein, said small HBV viral surface antigen and consensus numbers are as defined by Stuyver et al. (Stuyver et al., 2001).

With "codon" is meant a combination of 3 contiguous nucleotides which encode an amino acid according to the genetic code. A "codon" in the present invention furthermore can be comprised in a single-stranded (sense or antisense) or double-stranded (poly)nucleic acid. For deriving the amino acid sequence from an antisense strand, the corresponding sense strand (the inverted complement) needs to be used for translation into the corresponding amino acid sequence.

A large number of assays capable of detecting nucleotide sequences and nucleotide sequence polymorphisms (e.g. a mutation) is currently available. Some of these assays are based on physical methods whereas others use enzymatic approaches.

With "physical detection methods" is meant in the present context methods of nucleotied sequence polymorphism detection that require one or more physical processes for detection although not excluding the enzymatic process of prior PCR amplification of the target DNA sequence comprising one or more nucleotide sequence polymorphisms. Said physical processes include electrophoresis, chromatography, spectrometry, optical signal sensing and spectroscopy.

Physical nucleotide sequence polymorphism detection assays include electrophoretic methods such as SSCP, CDCE, CDGE, DGGE, TGGE, DGCE, nonisocratic CZE, TDGS, CSGE, MADGE and DSCA; chromatographic methods include DHPLC. Physical nucleotide sequence polymorphism detection assays may be effective for identification of known or new mutations and may require confirmation by direct DNA sequencing.

Single stranded conformation polymorphism (SSCP) is based on differences in mobility due to changes in sequence-dependent secondary and ternary structures of single stranded DNA. Critical for SSCP are the experimental conditions comprising gel temperature and gel composition. SSCP is a well-established and widely used assay reliable for DNA fragments having a size of or below 200 basepairs (bp). SSCP assays can be run in a gel or capillary electrophoresis format and can be combined with fluorescence-based detection of the ssDNAs (Kristensen et al., 2001; Nishimura et al., 2000; Bosserhoff et al., 1999; Iwahana et al., 1996). Constant denaturant capillary electrophoresis (CDCE) and constant denaturant gel electrophoresis (CDGE) are both based on differences in electrophoretic mobility between homo- and heteroduplex DNA molecules. Said differences in mobility depend on the differences in melting characteristics of said DNA duplexes. The melting of target DNA duplexes in CDCE and CDGE is implemented by using a zone of constant temperature and constant denaturant composition in the gel or capillary. CDCE and CDGE can be combined with fluorescence detection of the DNA molecules. CDCE can also be applied in the enrichment of rare mutants. The target DNA duplexes in CDCE and CDGE are typically 80 to 200 bp long (Khrapko et al., 2001; Kristensen et al., 2001; Li-Sucholeiki et al., 2000; Khrapko et al., 1997; Khrapko et al., 1994). In denaturing gradient gel electrophoresis (DGGE), melting of the target duplex DNA molecules is achieved by a low to high denaturant gradient in the polyacrylamide gel. In temperature gradient gel electrophoresis, said melting is achieved by a low to high temperature gradient. In double gradient capillary electrophoresis (DGCE), melting of the target homo- and heteroduplex DNA molecules is achieved by a chemical or thermal gradient and separated homo- and heteroduplex DNA is subsequently recompacted in a colinear second porosity gradient. Capillary zone electrophoresis (CZE) is also known as free-solution capillary electrophoresis (FSCE). Nonisocratic CZE, or thermal gradient capillary electrophoresis (TGCE), wherein a temperature gradient is generated internally in the capillary, can be used to separate target DNA homo- and heteroduplex molecules (Kristensen et al., 2001; Righetti et al., 1997). Two-dimensional gene scanning (TDGS) involves two-dimensional DNA electrophoresis comprising size separation in a first step and DGGE in a second step. TDGS allows detection of nucleotide polymorphisms in a set of target duplex DNAs of different size, e.g. obtained in a multiplex PCR reaction (Vijg et al., 1999). Addition of a GC-clamp (an artificial high-melting domain) to the end of a DNA fragment (incorporated via, e.g., a PCR primer) permits analysis of almost any DNA sequence in denaturing-based electrophoretic methods for detection of nucleotide polymorphisms (Sheffield et al., 1989; Myers et al., 1985). Microplate-array diagonal gel electrophoresis (MADGE) has been adapted to a (thermal) denaturing format and the detection of nucleotide polymorphisms was demonstrated with GC-clamped homo- and heteroduplex target DNAs (Day et al., 1998).

In conformation sensitive gel electrophoresis (CSGE), mildly denaturing conditions induce conformational changes in dsDNA which are different for homo- and heteroduplex target DNA. Hence, homo- and heteroduplex DNAs display a differential mobility during electrophoresis. CSGE can be adapted to allow fluorescence-based detection (Ganguly et al., 1998; Korkko et al., 1998).

Double-strand conformation analysis (DSCA) is a conformation-based mutation detection system wherein a known double-stranded reference DNA, labeled with fluorescein at a single strand (fluorescein-labeled reference or FLR DNA), is hybridized to unknown sample DNA. The difference in electrophoretic mobilities of the fluorescent homo- and heteroduplexes allows identification of nucleotide polymorphisms (Arguello et al., 1998). A similar technique is called HMA (heteroduplex mobility assay) but detection of DNA-duplexes relies on in gel staining of the DNA (Delwart et al., 1993). In HTA (heteroduplex tracking assay), a radiolabeled probe is annealed to a PCR product and the probe-PCR product heteroduplexes are separated by gel electrophoresis. A multiple-site-specific HTA has been described. (Resch et al., 2001; Delwart et al., 1994).

Separation of homo- and heteroduplex target DNA molecules by denaturing electrophoresis is described supra. Said separation can also be performed by denaturing liquid chromatography wherein temperature determines sensitivity. Denaturing high-performance liquid chromatography (DHPLC) can moreover be performed in monolithic capillary columns enabling the setting up of an array system. Fluorescence-based detection is possible, as well as on-line coupling to a mass spectrometer. The efficiency of nucleotide polymorphism detection by DHPLC can be increased by adding a GC-clamp to the end of the target DNA fragment (Huber et al., 2001; Narayanaswami et al., 2001; Xiao et al., 2001).

MALDI-TOF MS (matrix-assisted laser desorption-ionization time-of-flight mass spectrometry) has been succesfully used both as a direct DNA sequencing tool for DNA fragments under 100 bp and as a tool for detection of single nucleotide polymorphisms. Hybridization of allele-specific PNA-oligomers (peptide nucleic acid) with single stranded target DNA was proven to be highly compatible with MALDI-TOF MS analysis ((Griffin et al., 2000), and references therein).

With "enzymatic approaches for the generation of products signaling nucleotide sequence polymorphisms" is meant in the present context approaches relying on the activity of one or more enzymes for generation of said signaling products. Enzymes include DNA restriction endonucleases, DNA polymerases, DNA ligases, DNA/RNA structure-specific endonucleases, DNA/RNA flap endonucleases, DNA exonucleases and reverse transcriptases (RTs). Enzymatic approaches usually require a physical process (e.g. as described supra) for detection of the enzymatically produced signal.

Said enzymatic approaches include RFLP, AFLP, ASO-PCR, real-time PCR, LCR or LDR, CFLP, Invader assay, ddF, Bi-ddF, dnF, BESS and DNA minisequencing or sequencing. Some of these enzymatic approaches can be substituted for chemical or physical methodologies as will be discussed.

Restriction fragment length polymorphism (RFLP) is an assay producing a fingerprint of target DNA molecules by using one or more DNA restriction endonucleases. For detection of mutations or simple or single nucleotide polymorphisms, the target DNA is normally amplified via PCR (Schumm et al., 1988). In amplified fragment length polymorphism (AFLP), target DNA molecules are digested with a restriction endonuclease and the obtained fragments are amplified by PCR after ligation of adaptor sequences to said fragments (Vos et al., 1995). More specific enzymatic approaches to detect nucleotide sequence polymorphisms include PCR using allele-specific oligonucleotide (ASO) primers (ASO-PCR) in which the ASOs can discriminate between templates by virtue of their 3' terminal nucleotide. ASO-PCR can be improved by incorporating an additional deliberate mismatch adjacent to the 3' discriminating base which significantly reduces amplification of the template not comprising the discriminating 3' base of the ASO primer (Cha et al., 1992; Wu et al., 1989).

In real-time PCR, the progress of the PCR reaction can be followed in real-time and detection of mutants or nucleotide sequence polymorphisms is possible via monitoring annealing or melting curves of hybrizing or hybridized, respectively, DNA molecules. A number of real-time PCR setups is known comprising three types. In a first type real-time PCR, the amount of PCR product is determined by measuring fluorescence of a dsDNA staining dye such as SYBR Green I. If performed with ASO primers, this real-type PCR type could be utilized for detection of mutants or nucleotide sequence polymorphisms. The two other types of real-time PCR are based on the principle of fluorescence resonance energy transfer (FRET) between a light emitting label or donor or fluorophore and a label catching the light emitted by the donor, said light catching label known as acceptor or quencher or receptor. The acceptor can be fluorescent or non-fluorescent. If the acceptor also is fluorescent, the transferred energy can be emitted as a fluorescence characterisic of the acceptor. If the acceptor is not fluorescent, i.e. a quencher, then the energy is lost through equilibration with solvent. The acceptor-donor pair can be incorporated in two different oligonucleotides hybridizing adjacent (within 5 basepairs) to each other (hybridization probes) or in a single dual-labeled probe (exonuclease or 'TaqMan' probe and hairpin or 'Molecular Beacons' probe).

Two formats of hybridization probes furthermore exist. In the primer/probe format, the primer is labeled internally, usually with an acceptor dye, and the probe complementary to the primer extension product is 3'-end labeled, usually with a donor fluorophore. If the primer has the ASO-format or if the probe can discriminate between variants, than this real-time PCR-type can be used in detection of mutants or nucleotide sequence polymorphisms. In the probe/probe format, the donor and acceptor dyes are conjugated to the 5' and 3' ends of two different oligonucleotides. The 5' labeled probe is furthermore blocked at its 3' end to avoid extension by the polymerase. Either probe capable of discriminating between variants allows the use of the real-time PCR-type in detection of mutants or nucleotide sequence polymorphisms. A variation to the primer/probe or probe/probe format includes the use of two oligonucleotides (probe or primer), each having a different 'universal' tail. Said universal tails can hybridize to complementary universal probes, one labeled with an acceptor dye, the other one labeled with a donor dye. Both universal probes are brought in each other's proximity via the two universally-tailed oligonucleotides (probe or primer) hybridizing simultaneously to a common target and to said universal probes. Using this method with in conjunction with allele-specific primers (amplification format) or allele-specific probes (hybridization format) enables detection of nucleotide sequence polymorphisms (Beaudet et al., 2001).

Exonuclease or 'TaqMan' probes carry a fluorophore donor and a quencher acceptor, should hybridize in between the forward and reverse PCR primers, should be 100% hybridizing during the PCR primer extension step and should have a blocked 3' end (if not by the donor or the acceptor). During the PCR extension step, the Taq polymerase encountering the hybridized TaqMan probe will destroy said probe due to the polymerase's intrinsic 5'-3' exonuclease activity. Such, the fluorophore is separated from the quencher and increased fluorescence is the result. If said exonuclease probe can discriminate between variants, than it can be applied in real-time PCR-based detection of mutants or nucleotide sequence polymorphisms. The differences between exonuclease and hairpin probes include (i) the extension of the specifically hybridizing probe with complementary 5' and 3' tails (comprising 5 nucleotides or more) capable of forming a hairpin and (ii) the donor and quencher labels are attached to the 5' and 3' ends of the hairpin tails. Hybridization of the hairpin probe to the template results in spatial separation of the donor and quencher labels and, thus, in fluorescence. If hairpin probes can discriminate between variants, than they can be applied in real-time PCR-based detection of mutants or nucleotide sequence polymorphisms. Multiplex real-time PCR in either format, except for the format in which a dsDNA-staining dye is used, is possible using different donor-acceptor pairs and/or using primers or probes with different melting temperatures. (Bernard et al., 2001; Wittwer, 2001; Tyagi et al., 1998; Tyagi et al., 1996).

A hairpin primer comprising a Molecular Beacon-type structure, its loop, however, not binding to the target DNA and further comprising a 3' single stranded extension capable of hybridizing to the target DNA can be used for direct detection of the PCR amplified target DNA. Said amplification can be followed by measuring the increasing fluorescence as the hairpin is present in the amplicon in an open conformation. This hairpin primer-type is known as SUNRISE primers. Such hairpin primers can also be designed in the allele-specific format and can as well be used to prime rolling circle amplification of circularized padlock primers in conjunction with a second primer capable of priming complementary strand DNA synthesis (Faruqi et al., 2001; Nazarenko et al., 1997). Rolling circle amplification is explained in more detail infra. Another variation on the same theme is the one wherein the initial PCR cycle is primed with allele-specific primers comprising a 'universal' 5'-tail capable of hybridizing with a 'universal' tailed Sunrise-type probe. These 'universal', tailed hairpin primers are known as AMPLIFLUOR primers. Starting from the third cycle these Amplifluor primers act in priming DNA synthesis and starting from the fourth cycle synthesis of the strand complementary to the Amplifluor primer-primed ssDNA results in opening of the hairpin and, thus, the appearance of fluorescence (Myakishev et al., 2001).

A further modification of the hairpin primers described supra comprises the incorporation in the loop of the hairpin a sequence capable of hybridizing to part of the newly amplified target DNA. Amplification of the hairpin of the primer during PCR is prevented by incorporation of a blocking non-amplifiable monomer at the 3' end of the hairpin/5' end of the primer part. Said monomer is e.g. hexethylene glycol (HEG). Fluorescence is emerging after opening of the hairpin due to hybridization of the hairpin loop with the amplified target DNA. This type of hairpin primers is known as scorpion primers (Whitcombe et al., 1999).

Methods involving real-time measurement of the synthesis of a PCR product can also be modified such that said PCR product is measured only once, e.g., after the last PCR cycle. The latter method thus involves 'end-point' measurement of the PCR product.

Ligase chain reaction (LCR) or ligase detection reaction (LDR) uses a thermostable DNA ligase enzyme to ligate two pairs of complementary probes. Only in case of both the 3' end of the upstream probe and the 5' end of the downstream probe (which must be phosphorylated) matching perfectly with the target DNA, will the DNA ligase be capable of ligating said upstream and downstream probes. Thermal cycling of this process allows exponential amplification of the probe adducts. At least the *Thermus thermophilus* (Tth) DNA ligase discriminates mismatches at the 3'-side of the nick with greater efficiency than mismatches at the 5'-side of the nick. The fidelity of the Tth DNA ligase can be increased by incorporating an additional deliberate mismatch or a universal nucleoside (e.g. 3-nitropyrrole deoxyribonucleotide) at the position 2 bases upstream of the discriminating base. Mutant Tth DNA ligase with further increased fidelity (e.g. K294R and K294P variants) have been described. As a template for LCR or LDR, a PCR-amplified DNA target can be used. Multiplexing of LCR/LDR is possible using differently (fluorescently) labeled allele-specific probes and/or allele-specific probes of slightly different lengths. (Khanna et al., 1999; Luo et al., 1996; Barmy, 1991).

Variations of LCR have been described by Backman et al. (1991; EP0439182), said variations including the use of at least one modified probe. Variations include GAP-LCR wherein the gap between the upstream and downstream probes is filled by extension of the upstream probe by a DNA polymerase in the absence of the dNTP complementary to the 5'-end-base of the downstream probe. GAP-LCR can involve single or double gaps in 1 or 2 of the probe pairs, respectively. Gaps can also be filled by using additional gap-filling probes. Another probe modification involves introduction of overhanging modified ends (3' end of the upstream probe or 5' end of the downstream probe) such as a ribonucleotide tail which can be removed by a ribonuclease, or such as an abasic site which can be removed by specialized DNA endonucleases. LCR/LDR probes can also be adopted to the FRET format. As such, PCR and LCR are combined in a two-step thermal cycling sequence and allele-specific dye-labeled oligonucleotide ligation (DOL) is monitored in real time through FRET (Chen et al., 1998). Rolling circle amplification (RCA) involves a circularizable probe or padlock probe or open circle probe or C-probe (of at least 26 nucleotides) which incorporates at either end primers which, after annealing to a target DNA, can be ligated. Said padlock probe can be modified to a 'GAP-padlock probe' similarly as described for GAP-LCR. Using the 3'-terminal nucleotide as discriminating base, allele-specific circularization of the padlock probe is achieved. Circularized padlock probes are subsequently amplified using a (first) primer driving rolling circle amplification under isothermal or thermally cycling conditions. If a second primer complementary to e.g. the primer initiating RCA is added, then a mixture of hyperbranched DNA and released DNA fragments will be the result. A restriction enzyme site can be incorporated in the backbone loop of the padlock probe to convert the amplicon into monomers which can be detected after e.g. gel electrophoresis. Alternatively, the tandem DNA sequences can be decorated with specific labeled oligonucleotide tags. (Baner et al., 1998; Lizardi et al., 1998; Zhang et al., 1998; Nilsson et al., 1994).

A number of nucleotide sequence polymorphism detection assays are available which are based on the activity of a structure-specific endonucleases.

The first endonuclease-based nucleotide sequence polymorphism detection assay is CFLP or Cleavase Fragment Length Polymorphism. CFLP uses an engineered thermostable structure-specific endonuclease called Cleavase I (Third Wave Technologies Inc., Madison, WIS, USA). The formation of secondary structures recognized by Cleavase I are introduced in a DNA molecule, e.g. an amplicon obtained via PCR, by brief thermal denaturation followed by rapid cooling. It is clear that minor differences in sequence composition, e.g. single or simple nucleotide polymorphisms, between furthermore identical DNA molecules will give rise to different secondary structures. The Cleavase I fragments produced from said variant DNA molecules will thus constitute a different and species-specific DNA fingerprint. CFLP-fingerprinting has been used to perform e.g. genotyping of hepatitis C viruses (HCVs) present in biological samples (Sreevatsan et al., 1998). CFLP was also reported to be more robust and reproducible than e.g. SSCP or DDGE (De Francesco, 1998; Brow et al., 1996). A similar assay using the bacteriophage resolvase T4 endonuclease VII is known as EMD (enzymatic mutation detection; (Del Tito et al., 1998)). Both CFLP and EMD can be used with fluoresently labeled target DNA molecules. Fragments obtained through CFLP or EMD are subsequently resolved by gel or capillary electrophoresis. Other enzymes used in DNA heteroduplex cleavage assays include MutS, MutY and thymine glycosylase (Taylor, 1999). A similar type of assay exists for resolving RNA/RNA and RNA/RNA heteroduplexes. In case of RNA/RNA duplexes, the technique is called NIRCA (non-isotropic RNase cleavage assay) which includes synthesis of RNA from a DNA-dependent RNA polymerase promoter included in a primer previously used to amplify the target DNA by PCR. (Goldrick et al., 1996; Grange et al., 1990; Myers et al., 1985). Improvements to NIRCA have been disclosed by Faudoa et al. (Faudoa et al., 2000). An alternative chemical approach has been described as CCM (chemical cleavage of mismatch). Mismatched thymines and cytosines are chemically modified followed by piperidine-mediated cleavage of the dsDNA. CCM has been modified to be compatible with fluorescent detection and with solid phase capture of the heteroduplexes (Taylor, 1999; Rowley et al., 1995).

A second endonuclease-based nucleotide polymorphism detection assay is the Invader™ assay (Third Wave Technologies, Inc., Madison, Wis.) In the Invader™ assay, the DNA structure recognized by a thermostable flap endonuclease (FEN), is formed by an Invader probe that overlaps the signal probe by at least one base. The unpaired single-stranded flap of the signal probe is released during the FEN reaction and can be detected by various methods such as measuring fluorescence after capturing and extending the released signal probe flap with fluorescein-labeled nucleotides (ELISA-format), mass-spectrometry, denaturing gel electrophoresis, etc. The Invader™ assay was reported to detect mutant target in a mixture containing mutant/wild-type targets in a ratio of 1/1000. In order to discriminate between wild-type and variant (mutant or polymorphic; relative to wild-type) targets, Invader and signal probes are designed such that the cleavage site is the site of the variation. The Invader™ assay is independent of PCR and works equally well on DNA and RNA targets. (Lyamichev et al., 1999; Ryan et al., 1999; De Francesco, 1998).

A variation of the Invader™ assay is the Invader™ Squared FRET assay. In addition to the Invader and signal probes, a FRET (fluorescence resonance energy transfer) probe is required. The released signal probe fragment of the initial FEN reaction subsequently serves as an Invader probe invading the stem fragment of the hairpin formed intramolecularly in the FRET probe. This process induces a second FEN reaction during which the fluorophore in the FRET probe is separated from the nearby quenching dye in the FRET probe, resulting in the generation of fluorescence. Both FEN reactions occur at isothermic conditions (near the melting temperature of the probes) which enables a linear signal amplification. Alternatively, the loop of the FRET probe is omitted such that the released signal probe fragment of the initial FEN reaction is invading a partial dsDNA formed by the secondary target and a FRET probe complementary to the second target. The secondary target is optionally modified such that the last five nucleotides on the 3' end are 2'-O-methyl-RNA and such that it comprises a 3' $NH_2$ group. Optionally; an 2'-O-methyl RNA arrestor oligonucleotide which is complementary to the uncleaved primary signal probe is added to sequester the latter. Both options repress nonspecific background signal. The Invader Squared assay is applicable for detecting DNA as well as RNA targets. For detection of RNA targets, however, a modified endonuclease is required. (E is et al., 2001; Hall et al., 2000; Ledford et al., 2000).

Another variation of the Invader™ assay is the Invader™ Squared MALDI-TOF MS assay. In this assay the released signal probe fragment is not measured via a second FEN reaction releasing the fluorophore but via a second FEN reaction releasing biotin-labeled oligonucleotides which are characterized via MALDI-TOF MS (Griffin et al., 1999). Illustration of the use of the Invader assay applied to PCR amplicons was given by Mein et al. (Mein et al., 2000).

MIDAS (mutation identification DNA analysis system) is based on the annealing of a labeled probe to a target DNA. If a mismatch occurs (usually near the middle of said probe), the resulting heteroduplex can be cleaved at the mismatch site by a thermostable mismatch repair enzyme. The resulting probe fragments are thermodynamically less stable than the full-length probe and dissociate from the target DNA. A variety of probe fragment detection methods can be used. 'TaqMan'-type probes could be used in this system as well. (Bazar et al., 1999). For analyzing nucleotide sequence polymorphism in RNA target molecules, both ribozymes (hammerhead-, hairpin-, group I intron-, ribonuclease P- or hepatitis delta viral-type ribozymes) or deoxyribozymes ('DNAzymes') can be used. This feature is moreover the basis for the possible use of these enzymes as therapeutics or in gene therapy (Cairns et al., 2000; James at al., 1995).

Dideoxy fingerprinting (ddF) is a hybrid between Sanger dideoxy sequencing and SSCP. The Sanger reaction is performed with one labeled ddNTP and one primer, resulting in a set of nested 5' co-terminal DNA fragments. Said fragments are denatured and analyzed on a non-denaturing gel (i.e. SSCP). Disappearance of a band or appearance of a new band (both relative to the fingerprint of a reference target DNA) is indicative of the responsible underlying mutation. In bidirectional ddF (Bi-ddF), a sense and an antisense primer are used in the Sanger reaction. Bi-ddF can screen larger regions of target DNA for mutations. For DNA targets comprising GC-rich regions, ddF or Bi-ddF can be enhanced by combination with denaturing gel electrophoresis. The latter technique is called denaturing ddF or dnF. (Liu at al., 1998; Liu et al., 1996; Langemeier et al., 1994; Sarkar et al., 1992).

DNA minisequencing is a method based on the annealing of an unlabeled primer to a target DNA molecule and extension of the primer with a single labeled ddNTP. DNA minisequencing can be used for efficient screening of nucleotide sequence polymorphisms if the 3'-end of the primer is located immediately upstream of the polymorphic target nucleotide. The nature of the incorporated ddNTPs can be detected by electrophoresis, by MALDI-TOF, or in an array format in which either the target DNA(s) or the unlabeled primer(s) are immobilized to a solid support. Multiplexing of DNA minisequencing is possible. (Bray at al., 2001; Pastinen et al., 1997; Pastinen et al., 1996). Minisequencing can be combined with electronic detection via an electrode or piezoelectric crystal (Patolsky et al., 2001). Minisequencing can also be adopted to comply with the FRET format. The primer to be extended is labeled with e.g. a donor dye and the incorporated nucleotide is labeled with e.g. an acceptor dye. Fluorescence intensities of the dyes are subsequently determined (Chen et al., 1997). Another variation of minisequencing is GBA (Genetic Bit Analysis). First, a target DNA is amplified by PCR using a regular primer and a phosphorothioate-modified primer or otherwise modified primer resistant to a 5'-3' dsDNA-specific exonuclease. The dsDNA amplicon is subsequently converted into ssDNA by a 5'-3' dsDNA-specific exonuclease. The resulting ssDNA is then captured by an immobilized oligonucleotide of which the 3'-terminal nucleotide is adjacent to the polymorphic site and which is extended with a single nucleotide (Nikiforov et al., 1994). Minisequencing is also possible with RNA as template and using a reverse transcriptase enzyme (Pastinen et al., 2000). Base excision sequence scanning (BESS) is a technique involving incorporation of dUTP in an amplified target DNA molecule. Said target molecule is subsequently digested in the BESS-T-Scan reaction (Epicentre Technologies, Madison, Wis., USA) with an enzyme mix comprising uracil-N-glycosylase (UNG) and E. coli endonuclease IV. The action of both enzymes result in a cleavage of the DNA at the site of dUTP incorporation. In the BESS-G-TRACKER reaction (Epicentre Technologies, Madison, Wis., USA), deoxyguanosines are modified followed by enzymatic excision of the modified deoxyguanosines and cleavage of the DNA. Separation by gel electrophoresis of both reaction products results in T and G ladders analogous to those obtained via dideoxysequencing (see infra). Comparison with a reference DNA analyzed the same way allows identification of nucleotide sequences polymorphisms (Hawkins et al., 1999).

Still regarded as the 'gold standard' for determination of nucleotide sequence polymorphisms is direct DNA sequencing. One method of DNA sequencing is the method designed by Maxam and Gilbert (Maxam et al., 1977). The most common and widespread DNA sequencing method is based on the Sanger reaction or dideoxynucleotide chain termination reaction (Sanger et al., 1977). Sequencing primers can be labeled for detection of the terminated chains or internal labeling of the extension product is possible. Another DNA sequencing method is pyrosequencing. Here, the release of pyrophosphate (PPi) due to phosphodiester formation between two nucleotide-triphosphates. Released PPi is measured either via a secondary assay or via labeled phosphate (gamma-Pi or beta-Pi) in PPi wherein each of the four dNTPs carries a different label (see e.g. Williams 2000—WO00/36152; (Ronaghi et al., 1998)).

Cycle sequencing is based on the Sanger reaction but a thermostable polymerase is utilized. Contrary to PCR, a single primer is used in cycle sequencing. Due to the linear amplification of the target DNA, far less template DNA is required for cycle sequencing as compared to classical dideoxysequencing. Furthermore, the need to prepare single-stranded sequencing template is eliminated. ddNTPs can each be labeled with a different fluorescent tag ('dye terminators') allowing analysis of four reactions/dyes in a single gel lane. Alternatively, the label can be incorporated in the primer ('dye primers'). PCR (or RT-PCR) and sequencing can also be coupled in a single reaction, known as CAS (coupled amplification and sequencing), or a modification thereof known as CLIP which is run on the Visible Genetics Clipper sequencer which uses MICROCEL polyacrylamide gel cassettes. CLIP Sequencing enables single-tube, simultaneous determination of the nucleotide sequence from both directions of a PCR amplicon using two sequencing primers labeled with a different dye (Cy5 and Cy5.5). (Yager et al., 1999; Ruano et al., 1991).

In the near future, nanopore sequencing might also become available (Meller et al., 2000). Other DNA sequencing methods include molecular resonance sequencing which uses electrospray ionization (ESI) combined with Fourier transform ion cyclotron resonance (FTICR) mass spectrometry (Smith et al., 1994) and, for smaller DNA fragments, MALDI-TOF MS (cfr. supra). Diagnostic sequencing by combining specific cleavage of DNA followed by mass spectrometric analysis of the fragments has also been described (see e.g. Stanssens and Zabeau 2000—WO00/66771).

Another method of determining nucleotide sequence variations comprises dideoxynucleotide sequencing (Sanger reaction) wherein the regular dNTPs are replaced by modified dNTPs (such as alpha-thio dNTPs) that limit 3' exonuclease sensitivity of the extension product to the 3'-terminal dideoxynucleotide. The dideoxy-terminated ssDNAs are subsequently purified (e.g. via capturing them via a biotinylated sequencing primer) and hybridized to a known reference DNA. A proofreading polymerase, the unlabeled ddNTP of the primary sequencing reaction and the other three (differently) labeled ddNTPs are then added. In case of a 3' mismatch, the polymerase will exchange the unlabeled ddNTP for the correct matching labeled ddNTP. Alternatively, the secondary reaction comprises the proofreading polymerase and the same ddNTP as used in the primary reaction but modified such that it is resistant to 3' exonuclease activity. In perfectly matching primary extension products (relative to the reference DNA), the 3'-terminal ddNTP is replaced by the modified ddNTP whereas in 3' mismatching primary extension products, the 3'-terminal ddNTP is removed but not replaced by the modified ddNTP. The modified ddNTP is subsequently removed and the hybrids are further extended in the presence of regular dNTPs. The latter process is only occurring in case of an original 3' mismatch. Another variant of this method includes addition of regular dNTPs and a proofreading polymerase to the secondary reaction. Primary sequencing products with a mismatch (relative to the reference DNA) immediately 5' adjacent to the ddNTP will not be extended (the 3'-terminal ddNTP will be removed but the modified dNTP 5' adjacent to said ddNTP is resistant to 3' exonuclease activity). In yet another alternative, a Sanger-type reaction is performed in which a modified dNTP resistant to 3' exonuclease activity is used instead of a ddNTP. The resulting products are digested with a 3' exonuclease, the single strands purified and hybridized to a known reference DNA. Polymerase-mediated extension of said single strands will only occur if the modified dNTP is matching with the reference DNA. In all of the four variants mentioned, the banding pattern after separation of the final reaction products is indicative for the position and the nature of a nucleotide sequence polymorphism (Dahlhauser 2000—U.S. Pat. No. 6,150,105).

Yet another DNA sequencing methodology is known as SBH or sequencing-by-hybridization which uses an array of all possible n-nucleotide oligomers (n-mers) to identify n-mers comprised in an unknown DNA sample (Drmanac et al., 1993). Such high-density oligonucleotide arrays are useful for detecting DNA sequence polymorphisms as well, the array eventually becoming a VDA (variant detector array) (Sapolsky et al., 1999; Cronin et al. 1996; Hacia et al., 1996). Microscope slides can be replaced by optical fibers as solid support for the oligonucleotides (Healey et al., 1997). A variation of the above-described SBH is based on solution hybridization of probes with a known information region or information tags with the target DNA fragments to be sequenced. The information tag can be a DNA bar code (eventually comprising modified bases), a molecular bar code or a nanoparticle bar code and forms the basis for identification and characterization of the hybridized target DNA (Drmanac 2000—WO/0056937).

Said high-density oligonucleotide arrays or DNA chips abolish the need to design a set of oligonucleotides specifically hybridizing under the same conditions to a set of polymorphic nucleotide sequences. The latter approach is applied in conventional reverse blot assays by carefully adjusting length, polarity and position of the mismatched nucleotide(s) in the oligonucleotide probe (Saiki et al., 1989). Conventional reverse blot hybridization assays for genotyping and detection of nucleotide sequence polymorphisms have, however, been successfully commercialized, e.g. in the LiPA (Line Probe Assay) format (Innogenetics, Ghent, Belgium). (Stuyver et al., 1997; Stuyver et al., 1996).

Alternatively, ACRYDITE-modified oligonucleotide probes are copolymerized into a polyacrylamide gel. Single-stranded target DNA targets are electrophoresed through said gel and, depending on electrophoresis conditions (temperature and/or denaturant), captured by the oligonucleotides immobilized in a capture gel layer. This method is also applicable for detecting nucleotide sequence polymorphisms (Kenney et al., 1998).

Other hybridization-based methods for detecting nucleotide sequence polymorphisms include the solution phase sandwich hybridization assay in which the target DNA is captured by a target-specific immobilized capture probe and detected via an amplifier or linker probe. Two methods of signal generation have been described. A first one utilizes a branched oligonucleotide hybridizing to the flap of the linker probe not binding to the target DNA. Subsequently a labeled probe is hybridized to the branches of the amplifier probe and the amount of bound label is quantified. In a second method, a (partially) double stranded amplifier probe is hybridized to the flap of the linker probe not binding to the target DNA. The double stranded (part of) said amplifier probe comprises a promoter recognized by a DNA-dependent RNA polymerase. The signal generated is formed by newly transcribed RNA from the amplifier probe, the amount of which is quantified. (see e.g. Urdea 1991—WO91/10746).

Nucleotide sequence polymorphisms can also be detected by DASH (dynamic allele-specific hybridization) analysis which is based on melting curve analysis and measurement of to fluorescence while heating. This can be done on PCR products that are e.g. biotin-labeled and captured in microplate wells. Melting curves are established by measuring fluorescence of a ds-DNA-specific intercalating dye (Prince et al., 2001; Howell et al., 1999). Hybridization of a fluorescently labeled probe to a target DNA can also be measured by means of fluorescence polarization spectroscopy (Murakami et al., 1991).

"FRET" or "fluorescence resonance energy transfer" involves two dyes, a donor and acceptor dye, which are usually different. In such cases, FRET is detected by either fluorescence of the acceptor dye ('sensitized fluorescence') if said acceptor is itself fluorescent, or by quenching of the donor dye fluorescence if said acceptor is a quenching non-fluorescent dye. FRET can be delayed if the donor dye releases its fluorescence over time. This process is termed "TR-FRET" or "time-resolved FRET". Donor and acceptor dyes can also be the same in which case FRET is detected by the resulting fluorescence depolarization (Runnels et al., 1995). Dyes can also be covalently coupled to form a tandem fluorescent dye or tandem dye or tandem conjugate. E.g., a single donor dye is then capable of exciting two acceptor dyes simultaneously, leading to the emission of light of multiple wavelengths. For FRET to work, the donor emission wavelength profile should at least partially overlap with the acceptor absorption wavelength profile.

Commonly used fluorescent dyes include BODIPY FL, CY3, CY3.5, CY5, CY5.5, EDANS, FAM, fluorescein, HEX, IAEDANS, JOE, ORANGE GREEN, (LC) Red640, (LC) Red705, ROX, TAMRA, TET, tetramethylrhodamine and TEXAS RED.

Commonly used quencher dyes include BHQ-1, BHQ-2, BHQ-3, DABCYL, metal clusters such as gold nanoparticles (Dubertret et al., 2001) and QSY7.

Commonly used donor/acceptor pairs include fluorescein/ tetramethylrhodamine, fluorescein/fluorescein, fluorescein/ QSY7, fluorescein/LC RED640, fluorescein/LC Red705 IAEDANS/fluorescein, EDANS/DABCYL, BODIPY FL/BODIPY FL, FAM/BHQ-1, TET/BHQ-1, JOE/BHQ-1, HEX/BHQ-1, Oregon Green/BHQ-1, TAMRA/BHQ-2, ROX/BHQ-2, Cy3/BHQ-2, Cy3.5/BHQ-2, Texas Red/BHQ-2, Texas Red/BHQ-2, Cy5/BHQ-3 and Cy5.5/BHQ-3.

It will be clear to the skilled artisan that many variations and combinations can be made to the nucleotide sequence and nucleotide sequence polymorphism detection methods described supra. These are hereby incorporated in the present invention.

Based on the above explanation on methods for detecting nucleotide sequences and polymorphisms therein, the following further embodiments are included in the present invention.

The oligonucleotides according to the invention as described supra can be adapted such that they can be used in any of the methods for detection of nucleotide sequences or polymorphisms therein as described supra.

Thus, in an additional embodiment of the present invention, the oligonucleotide according to the invention further comprises a terminal extension and/or a hairpin structure, wherein said extension and/or hairpin structure is incorporated at either end or at both ends of said oligonucleotide. Said terminal extension is useful for, e.g., specifically hybridizing with another nucleic acid molecule, and/or for facilitating attachment of said oligonucleotide to a solid support, and/or for modification of said tailed oligonucleotide by an enzyme, ribozyme or DNAzyme.

In a further embodiment of the current invention, the oligonucleotide according to the invention is comprised within a padlock probe as described above or within a hairpin structure.

In another embodiment, the oligonucleotide of the present invention has a modification allowing detection and/or capturing of said oligonucleotide. Detection and/or capturing of said oligonucleotide furthermore enables detection and/or capturing of the target nucleic acid hybridized therewith. The interaction between said oligonucleotide and said target nucleic acid may be stabilized by cross-linking both via introduction of a cross-linking modification in said oligonucleotide and/or said target nucleic acid.

In yet another embodiment, the oligonucleotide of the invention comprises a 3'-terminal mismatching nucleotide and, optionally, a 3'-proximal mismatching nucleotide. Said oligonucleotides are particularly useful for performing polymorphism-specific PCR and LCR (or GAP-LCR).

Further comprised in the present invention is a composition comprising at least one oligonucleotide according to the description given supra.

It will be clear to the skilled artisan that any of the methods described supra for detecting nucleotide sequences and polymorphisms therein can be utilized for methods for detecting the presence of a HBV virus in a biological sample; and/or for detecting resistance to an antiviral drug of a HBV virus present in a biological sample; and/or for detecting the presence of a serine-encoding codon 204 or of a methionine-encoding codon 180 and a serine-encoding codon 204 of the HBV reverse transcriptase domain of a HBV virus present in a biological sample; and/or for detecting the presence of a valine-encoding codon 196 of the small HBV viral surface antigen open reading frame of a HBV virus present in a biological sample.

Therefor, the following aspects covering such detection methods and diagnostic kits, e.g. line probe assays, based on such detection methods are additionally included in the present invention.

One aspect of the invention relates to a method for detecting the presence of a HBV virus in a biological sample and/or a method for detecting resistance to an antiviral drug of a HBV virus present in a biological sample, said methods comprising the step of detecting the presence of a HBV polynucleic acid or fragment thereof according to the invention. A specific embodiment thereto includes said methods comprising the steps of
(i) obtaining a target HBV polynucleic acid from said biological sample wherein, said target HBV polynucleic acid is suspected to comprise a serine-encoding codon 204 of the HBV reverse transcriptase domain or to comprise a methionine-encoding codon 180 and a serine-encoding codon 204 of the HBV reverse transcriptase domain;
(ii) obtaining the nucleic acid sequence of the target HBV polynucleic acid of (i);
(iii) inferring, from the nucleic acid sequence obtained in (ii), the presence of said serine-encoding codon 204 of the HBV reverse transcriptase domain or of said methionine-encoding codon 180 and said serine-encoding codon 204 of the HBV reverse transcriptase domain and, therefrom, the presence of said HBV in said biological sample and/or said resistance to an antiviral drug of a HBV virus present in said biological sample.

Another specific embodiment thereto includes said methods comprising:
(i) obtaining a target HBV polynucleic acid present in said biological sample and/or obtaining the nucleotide sequence thereof;
(ii) when appropriate, partial or complete denaturation, or enzymatic modification, of the polynucleic acids obtained in step (i);
(iii) when appropriate, renaturation of the denatured polynucleic acids obtained in step (ii), preferably in the presence of at least one oligonucleotide according to the invention, and, if needed, including the step of enzymatically modifying, including extending, said oligonucleotide;
(iv) when appropriate, detection of the partially or completely denatured polynucleic acids obtained in step (ii), and/or of the hybrids formed in step and/or of the enzymatic modifications obtained in step (ii) and/or (iii);
(v) inferring, from the partially or completely denatured polynucleic acids, and/or from the hybrids, and/or from the enzymatic modifications, all detected in step (iv), and/or from the nucleotide sequence obtained in (i), the presence of said HBV virus in said biological sample and/or said resistance to an antiviral drug of a HBV virus present in said biological sample.

In yet another specific embodiment thereto, said methods are comprising:
(i) obtaining a target HBV polynucleic acid from said biological sample wherein said target HBV polynucleic acid is suspected to comprise a serine-encoding codon 204 of the HBV reverse transcriptase domain or to comprise a methionine-encoding codon 180 and a serine-encoding codon 204 of the HBV reverse transcriptase domain;
(ii) contacting the target HBV polynucleic acid of (i) with an oligonucleotide capable of discriminating a codon 204 encoding a serine from a codon 204 encoding a methionine, valine or isoleucine or with an oligonucleotide capable of discriminating a codon 180 encoding a methionine from a codon 180 encoding a leucine and an oligonucleotide capable of discriminating a codon 204 encoding a serine from a codon 204 encoding a methionine, valine or isoleucine;
(iii) inferring, from the discriminatory signal obtained in (ii), the presence of said serine-encoding codon 204 of the HBV reverse transcriptase or of said methionine-encoding codon 180 and of said serine-encoding codon 204 of the HBV reverse transcriptase domain and, therefrom, the presence of said HBV in said biological sample and/or said resistance to an antiviral drug of a HBV virus present in said biological sample.

In the latter methods, said discriminating in (ii) is based on hybridization and said discriminatory signal in (iii) is a hybridization signal.

With an "oligonucleotide capable of discriminating, in a (poly)nucleic acid, a codon encoding amino acid X1 (any amino acid) from a codon encoding amino acid X2 (any amino acid different from X1)" is meant an oligonucleotide yielding a signal when contacted with a (poly)nucleic acid comprising said codon encoding amino acid X1 but not yielding a signal when contacted with a (poly)nucleic acid comprising a codon encoding amino acid X2. Said signal, also referred to as "discriminatory signal", may be any signal obtainable by using said oligonucleotide in any of the assays capable of detecting nucleotide sequences and nucleotide sequence polymorphisms as described supra. Said signals include, e.g., fluorescent signals, (chemi)luminescent signals, radioactive signals, light signals, hybridization signals, mass spectrometric signals, spectrometric signals, chromatographic signals, electric signals, electronic signals, electrophoretic signals, real-time PCR signals, PCR signals, LCR signals, CFLP-assay signals and Invader-assay signals.

With "contacting an oligonucleotide with a (poly)nucleic acid" is generally meant annealing of said oligonucleotide with said (poly)nucleic acid or hybridizing said oligonucleotide with said (poly)nucleic acid. "Contacting an oligonucleotide with a (poly)nucleic acid" does not exclude and can thus further comprise enzymatic modification of said oligonucleotide wherein said modification may occur at the extremities of said oligonucleotide and/or internally in the nucleotide sequence of said oligonucleotide. Examples of enzymatic modifications of oligonucleotides are given in, e.g., the assays capable of detecting nucleotide sequences and nucleotide sequence polymorphisms described herein.

In another embodiment of the invention said methods further comprise, where applicable, aligning and/or comparing the obtained nucleic acid sequence with a set of HBV nucleic acid sequences contained within a database.

With "database" is meant in the present context a collection of nucleic acid or amino acid sequences, more specifically of HBV nucleic acid or amino acid sequences. A database is to be understood to comprise at least one nucleic acid or at least one amino acid sequence. A database can be recorded on a variety of carriers. Such carriers include computer readable carriers.

Comparison of sequences, e.g. determination of percent identity between sequences, and alignment of sequences can be performed using a mathematical algorithm. Determination of percent identity between sequences relies on a previous alignment of sequences. The percentage identity (and similarity) between sequences can be determined by using e.g. the GAP program (part of GCG, Genetics Computer Group, software; now available via Accelrys on http://www.accelrys.com). Alignments between sequences can e.g. be made using the ClustalW algorithm (e.g. part of GCG software or part of VNTI software distributed by InforMax Inc.). An alignment usually is a gapped alignment, i.e. the introduction of gaps in a sequence is allowed in order to optimize the alignment. A detailed statistical theory for gapped alignments has not been developed, and the best gap costs to use with a given substitution matrix are to be determined empirically. These algorithms make use of amino acid substitution matrices to detect similarities among sequences that have diverged (Altschul, 1991). Substitution matrices have also been applied to DNA sequence comparison (States et al., 1991). It will be clear to the one skilled in the art that the efficiency of aligning similar amino acid residues also determines the percentage of identity between sequences. A commonly used substitution matrix is the BLOSUM62 matrix. For particularly long and weak alignments, the BLOSUM45 matrix may be used. For alignment of short sequences, the older to PAM (percent accepted mutation)-matrices may be used (e.g. PAM30, PAM70). A good alignment of sequences with a larger evolutionary distance can be to obtained by using a PAM substitution matrix with a greater number (e.g. by using PAM100 instead of PAM40). The number after the BLOSUM matrix (e.g. BLOSUM62) refers to the minimum percent identity of the blocks used to construct the matrix; greater numbers are lesser distances. A database of sequences can be searched against using a nucleic acid or amino acid sequence of interest as 'query sequence'. Algorithms for searching databases are usually based on the BLAST software (Altschul et al., 1990) and comprise: 1) BLASTN, for searching a nucleic acid query sequence against a database of nucleic acid sequences; 2) BLASTP, for searching an amino acid query sequence against a database of amino acid sequences; 3) TBLASTN, for searching a amino acid query sequence against a database of translated nucleic acid sequences (translations in the six possible frames); 3) BLASTX, for searching a translated nucleic acid query sequence (translations in the six possible frames) against a database of amino acid sequences; and 4) TBLASTX, for searching a translated nucleic acid query sequence (translations in the six possible frames) against a database of translated nucleic acid sequences (translations in the six possible frames). For short query sequences, the expect value threshold is preferably set high, e.g. at 1000 for nucleotide sequences and at 20000 for amino acid sequences.

Another further embodiment relates to a method for detecting the amino acid encoded by codon 196 of the HBV small viral surface antigen open reading frame of a HBV virus present in a biological sample comprising detecting the presence of a HBV polynucleic acid according to the invention. In a specific embodiment thereto is included said method wherein said detected codon 196 encodes a valine. Said method may comprise the steps as described in the specific embodiments relating to the methods for detecting the presence of a HBV in a biological sample and/or for detecting resistance to an antiviral drug of a HBV virus present in a biological sample.

Another aspect of the current invention relates to a diagnostic kit for detecting the presence of a HBV virus in a biological sample and/or for detecting resistance to an antiviral drug of a HBV virus present in a biological sample, said kit comprising at least a means for detecting the presence of a HBV polynucleic acid according to the invention.

A specific embodiment thereto includes said diagnostic kit comprising:
(i) optionally, a means for obtaining the nucleic acid sequence of a target HBV polynucleic acid suspected to comprise a serine-encoding codon 204 of the HBV reverse transcriptase domain or to comprise a methionine-encoding codon 180 and a serine-encoding codon 204 of the HBV reverse transcriptase domain;
(ii) a means for infering, from the nucleic acid sequence obtained in (i), the presence of said serine-encoding codon 204 of the HBV reverse transcriptase domain or of said methionine-encoding codon 180 and said serine-encoding codon 204 of the HBV reverse transcriptase domain and, therefrom, the presence in said biological sample of said HBV.

In another specific embodiment, said diagnostic kit is comprising an oligonucleotide capable of discriminating, in said HBV polynucleic acid, a codon 204 encoding a serine from a codon 204 encoding a methionine, valine or isoleucine.

In a further specific embodiment, said diagnostic kit further comprises an oligonucleotide capable of discriminating, in said HBV polynucleic acid, a codon 180 encoding a methionine from a codon 180 encoding a leucine.

In yet another embodiment, said diagnostic kit is additionally comprising a means for detecting the discriminatory signal obtained by contacting said HBV polynucleic acid and said oligonucleotide or oligonucleotides.

Furthermore embodied are said diagnostic kits wherein said oligonucleotide or oligonucleotides are attached or immobilized to a solid support.

Another specific embodiment thereto includes said diagnostic kit comprising:
(i) a means for obtaining a target HBV polynucleic acid present in said biological sample and/or obtaining the nucleotide sequence thereof;
(ii) when appropriate, at least one oligonucleotide pair suitable for amplification of a target HBV polynucleic acid according to the invention;
(iii) when appropriate, a means for denaturing nucleic acids;
(iv) when appropriate, at least one oligonucleotide according to the invention;
(v) when appropriate, an enzyme capable of modifying a double stranded or single stranded nucleic acid molecule;
(vi) when appropriate, a hybridization buffer, or components necessary for producing said buffer;
(vii) when appropriate, a wash solution, or components necessary for producing said solution;
(viii) when appropriate, a means for detecting partially or completely denatured polynucleic acids and/or a means for detecting hybrids formed in the preceding hybridization and/or a means for detecting enzymatic modifications of nucleic acids;
(ix) when appropriate, a means for attaching an oligonucleotide to a known location on a solid support;
(x) a means for infering from the partially or completely denatured polynucleic acids and/or from the hybrids and/or from the enzymatic modifications, all detected in (viii), and/or from the nucleotide sequence obtained in (i), the presence of said HBV virus in said biological sample.

With "a means for infering, from a nucleic acid sequence, the presence of codon Y (Y is number as indicated) encoding amino acid X (X is amino acid as indicated)" is meant any technique or method to (i) localize in said nucleic acid sequence said codon Y, (ii) to translate said codon Y into the amino acid encoded by codon Y, and (iii) to conclude from (ii) if the amino acid encoded by said codon Y is the same as or is different from said amino acid X. Said means can include a method wherein (i) to (iii) all are performed manually, or wherein (i) to (iii) are performed computationally, or wherein any of (i) to (iii) are performed manually and/or computationally. Said means may include aligning and/or comparing an obtained nucleic acid sequence with a set of nucleic acid sequences contained within a database. Said means may furthermore include the result of (i) to (iii) being presented in the form of a report wherein said report can be in paper form, in electronic form or on a computer readable carrier or medium. Said means may furthermore include the searching of (nucleic acid and/or amino acid) sequence databases and/or the creation of (nucleic acid and/or amino acid) sequence alignments, the results of which may or may not be included in said report.

A further embodiment covers any of the above methods of the invention characterized further in that said methods are based on determining the nucleic acid sequence.

A further embodiment covers any of the above methods of the invention characterized further in that said methods are based on a hybridization assay.

A further embodiment covers any of the above methods of the invention characterized further in that said methods are based on a reverse hybridization assay.

A further embodiment covers any of the above diagnostic kits of the invention characterized further in that said diagnostic kits are based on determining the nucleic acid sequence.

A further embodiment covers any of the above diagnostic kits of the invention characterized further in that said diagnostic kits are based on a hybridization assay.

A further embodiment covers any of the above diagnostic kits of the invention characterized further in that said diagnostic kits are based on a reverse hybridization assay.

A further embodiment covers any of the above diagnostic kits of the invention characterized further in that said diagnostic kits are based on a line probe assay.

The invention further contemplates a method for detecting resistance to an antiviral drug of a HBV virus present in a biological sample, said method comprising the step of detecting the presence of a HBV DNA polymerase/reverse transcriptase protein or fragment according to the invention. Said detection may include the steps of determining the amino acid sequence of the HBV DNA polymerase/reverse transcriptase protein or from a part thereof obtained, e.g., after proteolytic digestion and separation of the resulting protein fragments via chromatographic and/or electrophoretic means. After electrophoresis, a protein fragment may be excised and eventually eluted from the gel before sequencing. Alternatively, the protein gel electrophoresis is combined with blotting whereby proteins are transfered to a membrane carrier (e.g. nitrocellulose, PVDF, nylon). The protein or protein fragment to be sequenced can in the latter case be excised from the membrane carrier. Alternatively, the HBV DNA polymerase/transcriptase protein according to the invention is detected using an antibody specifically recognizing the serine at position 204 of the HBV reverse transcriptase domain. In particular, said antibody should not recognize a methionine, valine or isoleucine at said position 204. In yet another alternative, the HBV DNA polymerase/reverse transcriptase according to the invention is detected phenotypically, i.e. said HBV DNA polymerase/transcriptase may display a unique pattern of antiviral drug sensitivity not shared with HBV DNA polymerase/reverse transcriptases comprising a codon 204 encoding a methionine, valine or isoleucine. Phenotypic detection of the HBV DNA polymerase/reverse transcriptase according to the invention thus includes e.g. the steps of determining the sensitivity of an activity of a HBV DNA polymerase/reverse transcriptase from a HBV virus present in a biological sample to a panel of antiviral drugs. Alternatively, the HBV DNA polymerase/reverse transcriptase from a HBV virus present in a biological sample and suspected to comprise a polynucleic acid according to the invention is produced in a recombinant system and the sensitivity to a panel of antiviral drugs is determined of an activity of the recombinantly expressed HBV DNA polymerase/reverse transcriptase.

It will be clear to the skilled artisan that a vector system enabling HBV viral replication or enabling production of a HBV-encoded protein, or a functional part thereof, is suited for testing or assaying the effect of an antiviral drug on the HBV viral replication or function of the HBV-encoded protein (or part thereof), respectively. In particular, such assays can be performed with a mutant HBV polynucleic acid according to the present invention or with a mutant HBV DNA polymerase or mutant HBsAg protein according to the present invention. The results of such assays can be compared to results of similar assays performed with wild-type HBV polynucleic acids or wild-type HBV proteins, or functional parts thereof. A person skilled in the art will appreciate that the HBV DNA polymerase/reverse transcriptase has multiple recognized biological/biochemical functions including primase activity, reverse transcriptase activity (RNA-dependent DNA polymerase activity), DNA polymerase activity (DNA-dependent DNA polymerase activity) and RNAse (RNAse H) activity and is furthermore involved in the interaction with the core antigen protein (HBcAg) and in the encapsidation of the viral DNA. Wild-type or mutant HBV DNA polymerase can be isolated from HBV particles present in a patient's serum or can be produced by e.g. a stably transformed hepatoma cell line. Alternatively, said HBV DNA polymerase is expressed and produced in a heterologous system (e.g. *S. cerevisiae*) or by using a baculovirus expression system, a mitochondrial translation system (e.g. as described in U.S. Pat. No. 6,100,068) or in a cell-free system, e.g. a rabbit reticulocyte lysate coupled transcription-translation system (Li et al., 1999). Mutant HBV DNA polymerase DNA sequences can be produced by in vitro mutagenesis. Substantial purification of produced HBV DNA polymerase/reverse transcriptase can be achieved if e.g. a heterologous epitope (e.g. the FLAG epitope, cfr supra) is introduced in or fused to said HBV DNA polymerase/reverse transcriptase. Said epitope allows purification of the HBV DNA polymerase/reverse transcriptase e.g. on an affinity column containing immobilized anti-heterologous epitope antibodies (e.g. anti-FLAG M2 monoclonal antibodies). Alternatively, the recombinant HBV polymerase/reverse transcriptase is part of fusion protein, said fusion protein further comprising e.g. a histidine-tag, a carbohydrate-binding moiety (e.g. lectin, maltose binding protein) or beta-galactosidase. Substantial purification of said fusion protein is achievable by e.g. metal-affinity chromatography (in case a histidine-tag is present), carbohydrate-affinity chromatography (in case a carbohydrate-binding moiety is present) or immuno-affinity chromatography using an anti-body against the protein fused to the HBV DNA polymerase/reverse transcriptase, e.g. beta-galactosidase. Optionally, said fusion protein is cleavable by a suitable protease (e.g. protease factor Xa) such that the HBV DNA polymerase/reverse transcriptase is obtainable separated from the other moiety of the fusion protein, e.g. by another round of purification as described supra. Alternatively, HBV viral particles are isolated from a biological sample by techniques such as affinity capture (e.g. using antibodies against the HBV viral surface antigen or using a protein receptor to said surface antigen or anti-idiotypic antibodies to said protein receptor, cfr. infra) or gradient centrifugation. HBV viral particles obtainable via these or other ways are further amenable to analysis e.g. of the HBV DNA polymerase/reverse transcriptase or of the HBV nucleic acids. In yet another alternative, the multiprotein replicating core complex or intracellular replicating core are purified from infected liver cells and the obtained preparations comprising the HBV DNA polymerase/reverse transcriptase are used to assay the functions and activities of the HBV DNA polymerase/reverse transcriptase (Urban et al., 2000). Clearly, said purification of viral particles or of the replicating core complex can be applied to obtain said particles or core complex from cells infected with HBV variants comprising the mutations of the present invention.

Improved conditions for assaying viral reverse transcriptase activity have been described (Bird and Chang-Yeh in U.S. Pat. No. 5,817,457) and include acidic pH and elevated temperatures. Reaction conditions for assaying activity of RNAse H derived from the HBV DNA polymerase/reverse transcriptase have been described by e.g. Yoon et al. in U.S. Pat. No. 6,071,734. Assay conditions to determine primase-, polymerase-, and reverse transcriptase activity of in vitro produced HBV DNA polymerase/reverse transcriptase, or fragments thereof, have been described by Li et al. (Li et al., 1999). Assays to determine protein-protein interaction, e.g. interaction between the HBV DNA polymerase/reverse transciptase and HBcAg, include two- and three-hybrid assays and real-time biomolecular interaction analysis (BIA). With "two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins, termed "bait" and "prey", with one of said proteins fused to DB and the other of said proteins fused to AD, and with said two proteins being capable of physical interaction, are able to re-unite the DB and AD domains of the transcription factor which results in target gene expression. The target gene in the yeast two-hybrid assay is usually a reporter gene such as the beta-galactosidase gene. Interaction between protein partners in the yeast two-hybrid assay can thus be quantified by measuring the activity of the reporter gene product (Bartel et al., 1997). Alternatively, a mammalian two-hybrid system can be used which includes e.g. a chimeric green fluorescent protein encoding reporter gene (Shioda et al., 2000). Yet another alternative consists of a bacterial two-hybrid system using e.g. HIS as reporter gene (Joung et al., 2000). A three-hybrid interaction assay has been described by e.g. Liu and Licitra in U.S. Pat. No. 5,928,868. "BIA" is a technology for studying in real time conditions the interaction between biomolecules without labelling of the interacting biomolecules. The interaction between biomolecules is measured as changes in surface plasmon resonance (SPR) spectra. The BIA-technology can not only be used to study protein-protein interactions but can likewise be utilized to study interaction between e.g. proteins and polynucleic acids, hormones and their receptor, antiviral drugs and their target, and can as well be used to study the effect of compounds on such interactions, e.g. as a screening method to find inhibitors of such interactions (Nishikawa et al., 1999; Medaglia et al., 1998; Fitz et al., 1998).

Another additional aspect of the invention comprises an assay determining the effect of an antiviral drug on the function of a mutant HBsAg according to the present invention. A person skilled in the art will appreciate that the HBV HBsAg has multiple recognized biological/biochemical functions including functions in viral attachment/entry into the host cell (i.e. a role in infectivity of HBV), in viral particle assembly and in the secretion of viral particles. HBsAg is furthermore a target of the host's immune system and 'escape' mutants have been reported. The antibody against HBsAg, HBIg, is often used as a passive immunization means in patients that have undergone a liver transplant. Wild-type or mutant HBsAg can be obtained as described supra for HBV DNA polymerase. Alternatively, HBsAg is recovered by affinity interaction with antibodies against HBsAg or with a HBsAg receptor protein or with an anti-idiotypic antibody to said HBsAg receptor protein, said reported receptor proteins including monomeric and polymeric human albumin (Eibl et al. in U.S. Pat. No. 5,576,175 and Machida et al., 1984, respectively) and endonexinII/annexinV (Yap in European Patent No EP0672136). HBV and HDV (hepatitis delta virus) viral particles may be isolated from a biological sample by techniques such as affinity capture e.g. using antibodies against the HBV viral surface antigen or using a receptor to the HBV viral surface antigen or anti-idiotypic antibodies thereto.

In an alternative aspect of the invention, activity of a HBV DNA polymerase/reverse transcriptase, including the mutant HBV DNA polymerase/reverse transcriptases of the invention, or the sensitivity thereof to antiviral compounds is assayed in host cells containing a conditional mutation in the endogenous DNA polymerase. As such, expression of the HBV DNA polymerase/reverse transcriptase can possibly rescue growth of said mutant host cells under restrictive conditions. Sensitivity of the HBV DNA polymerase/reverse transcriptase to antiviral compounds can be assayed by measuring the extent of growth of said mutant host cells under restrictive conditions and in the presence of an antiviral compound. Said growth is subsequently compared to growth of said host cells under restrictive conditions and in the absence of said antiviral compound.

In a further alternative aspect of the invention is included the use of mutant HBV particles, including HBV particles comprising a mutant DNA according to the present invention, to infect non-human animals which are useful as a model for human HBV infection or as a model for evaluating anti-HBV compounds, therapies and prohylaxes. Said model non-human animals have been described, e.g. by Reisner in U.S. Pat. Nos. 5,849,987 and 5,858,328.

Many antiviral drugs against HBV (HBV antiviral drugs) are known and include: lobucavir, penciclovir or famciclovir, lamivudine (3TC; beta-L-(−)-2',3'-dideoxy-3'-thiacytidine), interferon-alpha, adefovir dipivoxil (Bis-POM-PMEA) or adefovir (PMEA; 9-(2-phosphonyl-methoxyethyl)-adenine), entecavir (BMS 200475), emtricitabine [(−)FTC; (−)-beta-L-2',3'-dideoxy-5-fluoro-3'-thiacytidine], DXG [(−)-beta-D-2,6-diaminopurine dioxolane], DAPD (diaminopurine dioxolane), clevudine (L-FMAU; 2'-fluoro-5-methyl-beta-L-arabinofuranosyluracil), L-dT (beta-L-thymidine), L-Fd4C (2',3'-dideoxy-2',3'-didehydro-beta-L(−)-5 fluorocytidine), foscarnet, carbovir, racivir, ganciclovir, tenofovir, nevirapine, (−) BCH189 (Ono et al., 2001), QYL865 (Fu et al., 2000), thymosin-alpha, and HBIg. Two or more HBV antiviral drugs can be used in combination as well.

A further aspect of the invention thus includes a method for screening for drugs active against a HBV virus comprising a polynucleic acid according to the invention or comprising a HBV DNA polymerase/reverse transcriptase according to the invention, said method comprising:
 (i) measuring replication of said HBV virus in the absence of said drug;
 (ii) measuring replication of said HBV virus in the presence of said drug;
 (iii) inferring from (i) and (ii) the inhibitory effect of said drug on replication of said HBV virus.

In a specific embodiment thereto, said method is further comprising performing steps (i), (ii) and (iii) with a wild-type HBV virus and comparing the inhibitory effect of said drug on replication of said wild-type HBV virus with the inhibitory effect of said drug on replication of said HBV virus comprising a polynucleic acid according to the invention. In yet another further embodiment thereto are included said methods further comprising obtaining said HBV virus from a biological sample.

Yet another further embodiment of the invention includes a method for screening for drugs active against a HBV virus comprising a polynucleic acid according to the invention or comprising a HBV DNA polymerase/reverse transcriptase according to the invention, said method comprising:
(i) measuring a DNA polymerase/reverse transcriptase activity of said HBV virus in the absence of said drug;
(ii) measuring the same DNA polymerase/reverse transcriptase activity as in (i) of said HBV virus in the presence of said drug;
(iii) inferring from (i) and (ii) the inhibitory effect of said drug on said DNA polymerase/reverse transcriptase activity of said HBV virus.

In a specific embodiment thereto is included said method further comprising performing steps (i), (ii) and (iii) with a wild-type HBV virus and comparing the inhibitory effect of said drug on a DNA polymerase/reverse transcriptase activity of said wild-type HBV virus with the inhibitory effect of said drug on said DNA polymerase/reverse transcriptase activity of said HBV virus comprising a polynucleic acid according to the invention. In yet another further specific embodiment thereto are included said methods further comprising obtaining said HBV virus from a biological sample. With "a DNA polymerase/reverse transcriptase activity" is meant either one of the biological or biochemical activities of the HBV DNA polymerase/reverse transcriptase as mentioned supra.

The current invention further relates to isolated HBV variants comprising a mutation identified in the present invention or comprising a combination of mutations identified in the present invention.

Thus, in one embodiment of the invention is included an isolated HBV variant comprising the M204S mutation in codon 204 of the HBV reverse transcriptase domain.

In another embodiment is included an isolated HBV variant comprising the L180M and M204S mutation in codons 180 and 204, respectively, of the HBV reverse transcriptase domain.

Another embodiment covers an isolated HBV variant comprising the W196V mutation in codon 196 of the HBV small viral surface antigen open reading frame.

In another embodiment is included an isolated HBV DNA polymerase/reverse transcriptase comprising the M204S mutation.

In yet another embodiment is included an isolated HBV DNA polymerase/reverse transcriptase comprising the L180M and M204S mutation.

Another further embodiment covers an isolated HBV small viral surface antigen, or parts thereof, comprising the W196V mutation. A further embodiment thereto includes HBV middle and large viral surface antigen comprising said HBV small viral surface antigen or said part thereof.

Yet another embodiment of the invention relates to the use of said isolated HBV variants and/or said isolated HBV small viral surface antigen, or said part thereof, and/or said HBV middle and/or large viral surface antigens as therapeutic compounds or vaccines active against HBV and/or HDV infection. In a specific embodiment thereto, said isolated HBV small viral suface antigen, or said part thereof, and/or said HBV middle and/or large viral surface antigens are modified.

Said antigens clearly are proteins. The terms "protein", "peptide" or "oligopeptide", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues. A number of said amino acid modifications can occur as a result of post-translational modification as will be recognized by the one skilled in the art. Other modifications include the addition of a chemical group to one or more amino acids of a protein, peptide or oligopeptide. Said chemical groups include e.g. biotin. Proteins, peptides or oligopeptides can furthermore generally be labeled radioactively, chemiluminescently, fluorescently, phosphorescently, with infrared dyes or with a surface-enhanced Raman label or plasmon resonant particle.

In a further embodiment, said therapeutic compounds or vaccines active against HBV and/or HDV infection comprise at least one of said isolated HBV variants and/or said isolated HBV small viral suface antigens, or said parts thereof, and/or said HBV middle and/or large viral surface antigens. In a specific embodiment thereto, said therapeutic compounds or vaccines further comprise a negatively charged phospholipid.

Yet another further embodiment of the invention relates to the use of said isolated HBV variants and/or said isolated HBV small viral surface antigen, or said parts thereof, and/or said HBV middle and/or large viral antigens in the manufacture of therapeutic compounds or vaccines active against HBV and/or HDV infection.

The invention further embodies antibodies and anti-idiotypic antibodies against said isolated HBV variants and/or said isolated HBV small viral surface antigen, or said parts thereof, and/or said HBV middle and/or large viral antigens. In a specific embodiment thereto, said antibodies are monoclonal antibodies. In a further specific embodiment, said antibodies are humanized monoclonal antibodies.

Further embodied in the invention is the use of said antibodies in immunological methods for detecting said HBV variants and/or said HBV small viral surface antigen, or said parts thereof, and/or said HBV middle and/or large viral antigens in a biological sample. In a specific embodiment thereto, said antibodies are used in a method for diagnosing HBV and/or HDV infection. In a further embodiment, said antibodies are part of a diagnostic kit capable of detecting HBV and/or HDV infection.

In another embodiment of the invention is covered the use of a method of the invention or a diagnostic kit of the invention to follow progression of HBV, and possibly HDV, infection.

A further embodiment covers the use of a method of the invention or a diagnostic kit of the invention to monitor the occurrence of resistance to an antiviral drug.

Another further embodiment covers the use of a method of the invention or a diagnostic kit of the invention to adapt a therapeutic regimen against HBV, and possibly HDV, infection due to the occurrence of resistance to an antiviral drug.

“Antibodies” include monoclonal, polyclonal, synthetic or heavy chain camel antibodies as well as fragments of antibodies such as Fab, Fv or scFv fragments. Monoclonal antibodies can be prepared by the techniques as described in e.g. Liddle et al. (Liddle et al., 1991) which comprise the fusion of mouse myeloma cells to spleen cells derived from immunized animals. Furthermore, antibodies or fragments thereof to a molecule or fragments thereof can be obtained by using methods as described in e.g. Harlow et al. (Harlow et al., 1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibodies can generally be labeled radioactively, chemiluminescently, fluorescently, phosphorescently, with infrared dyes or with a surface-enhanced Raman label or plasmon resonant particle. Antibody labels include alkaline phosphatase, PKH2, PKH26, PKH67, fluorescein (FITC), Hoecst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA (enyme-linked in assay), RIA (radio-immuno-assay) and LIA (line immunoassay), to immunoaffinity purification of proteins, immunoprecipitation of proteins and immunolocalization of proteins.

EXAMPLES

The following examples only serve to illustrate the present invention. These examples are in no way intended to limit the scope of the present invention.

Example 1

Hepatitis Serology and HBV DNA Assay

HBsAg, anti-HBs, HBeAg, anti-HBe, and anti-HCV were determined by the microparticle enzyme-immunoassay (META) method (Abbott Laboratories, North Chicago, Ill., US). Anti-HDV enzyme-immunoassay method was performed as per the methodology supplied by the manufacturer (Abbott Laboratories, North Chicago, Ill., US). Serum levels of HBsAg were determined by a modified Laurell electrophoresis system (Gerlich et al., 1975). HBV-DNA levels were tested by using a commercial liquid-hybridization assay (Digene, Maryland, US), with the lower limit of detection of this assay 5 pg/mL of viral DNA.

Example 2

History of the Patient

The patient was a 56-year-old Caucasian male with known HBV infection since 1990, diagnosed during a routine checkup. A liver biopsy in 1996 revealed chronic active hepatitis (CAH) with a histological activity index (HAI) of 8 according to Knodell et al. (Knodell et al., 1981). He was HBeAg negative, anti-HBe positive and as well as positive for HBV DNA by PCR. IFN therapy, 5 MU/TIW (5 million units/three times in one week), was initiated in March 1997. The patient did not show an ALT (alanine amino-transferase) decrease or virological response (HBV DNA level was 74 pg/mL at the end of IFN treatment). After 8 months of treatment, the patient discontinued IFN therapy and began taking lamivudine, 150 mg/day. During lamivudine treatment, there was normalization of ALT and replication inhibition of HBV. At month 18 of lamivudine treatment, however, clinical breakthrough occurred, characterized by an ALT flare and detection of HBV DNA by a hybridization assay. Lamivudine was continued, and IFN (9 MU/TIW) was added one year after the development of clinical breakthrough. This combination therapy led to normalization of liver enzymes, however, HBV DNA levels remained high during this period. IFN was stopped after 12 months of addition and lamivudine was discontinued after 2 months of IFN withdrawal. An ALT flare was observed following the cessation of lamivudine treatment. The Met204Ser mutation in the HBV DNA polymerase/reverse transcriptase was detected along with the Leu180Met mutation in all 7 samples obtained since the development of lamivudine resistance and 3 samples obtained after cessation of lamivudine treatment. The YSDD pattern persisted and did not replace with the wild type patterns during the period that the patient stopped all antiviral medications. An ALT flare and increase in HBV DNA replication were observed after cessation of lamivudine treatment. One important feature of this novel mutation may be its persistence and dominance over the wild type strain even after lamivudine discontinuation, which is in contrast to the conventional mutations where a reversal to wild type strain is observed after stopping lamivudine. The lamivudine treatment was re-started again at 8 months after stopping antiviral medications. HBV DNA levels did not show any change but ALT levels showed a significant decrease. The serum sample obtained at the 3th month of lamivudine re-treatment also yielded a YSDD pattern.

The HBsAg level of the patient was 1.19 µg/mL at the beginning of the lamivudine treatment and became undetectable after 4 months. HBsAg level increased to 10.8 µg/mL just after breakthrough virus emerged. After addition of IFN to lamivudine treatment, HBsAg levels were found as 18.3 µg/mL, 9.3 µg/mL, and 10.3 µg/mL in subsequent three determinations. Following discontinuation all medication, the HBsAg level remained comparable to the previous last measurements at 7.1 µg/mL.

A schematic overview of the patient's history is given in FIG. 1.

Example 3

Extraction of HBV-DNA

HBV DNA was extracted from 150 µL serum which was incubated mixed with 300 µL lysis buffer (20 mM Tris HCl, pH 8.0, 10 mM EDTA, 0.1% SDS) and 50 µL proteinase K (at 10 mg proteinase K/mL). The mixture was incubated at 60° C. for 4 hr. Incubation was followed by extraction with 400 µL phenol/chloroform. The DNA-containing phase was subsequently extracted with 400 µL chloroform/isoamylalcohol (24/1). DNA was precipitated overnight at −20° C. or −80° C. after adding 500 µL ethanol (96% ethanol containing 0.3 M NaCl) and 10 µL tRNA (at 1 mg tRNA/mL). The DNA was subsequently collected by centrifugation. The pelleted DNA was washed with 1 mL 75% ethanol. Finally, the DNA was resuspended in 20 µL distilled water (DNAse- and RNAse-free).

Example 4

PCR Amplification of the Reverse Transcriptase Domain of the HBV DNA Polymerase/Reverse Transcriptase Open Reading Frame Five microliters of the DNA samples as obtained in Example 2 were made up to 50 µL with a PCR mixture containing 10 mM Tris HCl, pH 8.3, 50 mM KCl, 1.5 mM $MgCl_2$, 100 mM dNTP, 25 µmol/µL of sense and anti-sense primers and 2.5 Units of Taq DNA polymerase. To amplify the HBV polymerase gene, a first PCR consisting of 35 cycles of denaturation at 94° C. for 1 min, primer annealing at 45° C.

for 1 min and chain extension for 2 min at 72° C. was performed. The conditions for the nested PCR were the same as those for the first PCR using 5 μL of the sample from the first PCR as template. A pair of nested primers (nested relative to the PCR product obtained during the first round of PCR) was used to increase the yield of HBV polymerase PCR product. Outer primers were (i) sense 5'-CAC CTGCAGCCTCATTTTGTGGGTCACCATA-3' (SEQ ID NO:7) and (ii) antisense 5'-CAT AAGCTTCACAATTCGTTGACATACTTTCCAAT-3' (SEQ ID NO:8), and nested primers were (iii) sense 5'-GTG CTGCAGTTTGTGGGTCACCATATTCTTG-3' (SEQ ID NO:9) and (iv) antisense 5'-GAC AAGCTTTTGACATACTTTCCAATCAATAG-3' (SEQ ID NO:10). The nucleotides underlined in the primer nucleotide sequences denote restriction enzyme recognition sites for Pst I ("CTGCAG") or Hin dIII ("AAGCTT"). By using the nested sense primer and the nested antisense primer, nucleotides 360 to 480 of the HBV DNA polymerase were amplified.

Example 5

Direct Sequencing of PCR Products

PCR products as obtained in Example 4 were purified by the isopropanol precipation method. Direct sequencing of the PCR products was performed with the dye terminator cycle sequencing kit (Applied Biosystems, US) using the nested PCR primers. Both strands of each PCR product were sequenced. The reaction products were run on the ABI 310 automated sequencer (PE, Applied Biosystems, US). Generated sequences were compared with the sequence of a HBV genotype D published in Genebank (Genebank accession number X02496; SEQ ID NO:3), which is the dominant genotype in Mediterranean region and Turkey (Bozdayi et al., 2001). In FIG. 2, the amino acid sequence of the HBV DNA polymerase derived from Genbank accession number X02496 (SEQ ID NO:1) is aligned with the amino acid sequence derived from the HBV DNA polymerase isolated from patient 7 (SEQ ID NO:4). From FIG. 2 it is clear that the HBV DNA polymerase isolated from patient 7 carries two mutations, the already known Leu180Met mutation and the novel mutation Met204Ser. As stated in the introductory section, the open reading frames of the HBV DNA polymerase gene and the HBV surface antigen gene are partially overlapping. In FIG. 3, the amino acid sequence of the HBsAg derived from Genbank accession number X02496 (SEQ ID NO:2) is aligned with the amino acid sequence derived from the HBsAg isolated from patient 7 (SEQ ID NO:5). From FIG. 3 it can be derived that the mutation Met204Ser in the HBV. DNA polymerase of patient 7 also results in the occurrence of a mutation, Trp196Val of the HBV HBsAg. FIG. 4 shows an alignment of the nucleotide sequence of the HBV DNA polymerase as defined by Genbank accession number X02496 (SEQ ID NO:3) with the nucleotide sequence of the HBV DNA polymerase region of patient 7 as determined in this study (SEQ ID NO:6). Numbering of the nucleotides in FIG. 4 is based on the numbering of the DNA sequence as defined in Genbank accession number X02496. The mutations Met204Ser (HBV DNA polymerase) and Trp196Val (HBsAg) are both caused by mutations at the nucleotide level of nucleotides 742 (T to G) and 743 (G to T). The additional nucleotide mutations in the HBV DNA isolated from patient 7 (nucleotides 669, 816 and 884, see FIG. 4) are silent mutations and are not causing mutations in the amino acid sequence of the HBV DNA polymerase.

An amino acid numbering convention for the RT domain of the human HBV polymerase and for the HBsAg as proposed in a recent study (Stuyver et al. 2001) was used to overcome inconsistencies resulting from the reference of mutations in different HBV genotypes.

REFERENCES

Altschul, S. F. (1991) J. Mol. Biol. 219, 555-565
Altschul, S. F., Gish, W., Miller, W., Myers, E. W. & Lipman, D. J. (1990) J. Mol. Biol. 215, 403-410
Arguello, J. R., Little, A. M., Pay, A. L., Gallardo, D., Rojas, I., Marsh, S. G., Goldman, J. M. & Madrigal, J. A. (1998) Nat Genet. 18, 192-194
Barter, J., Nilsson, M., Mendel-Hartvig, M. & Landegren, U. (1998) Nucleic Acids Res 26, 5073-5078
Barany, F. (1991) Proc Natl Acad Sci USA 88, 189-193
Bartel, P. L. & Fields, S. (1997) The yeast two-hybrid system. Oxford University Press, Bazar, L. S., Collier, G. B., Vanek, P. G., Silas, B. A., Kow, Y. W., Doetsch, P. W., Cunningham, R. P. & Chirikjian, J. G. (1999) Electrophoresis 20, 1141-1148
Beaucage, S. L. (2001) Curr Med Chem 8, 1213-1244
Beaudet, L., Bedard, J., Breton, B., Mercuri, R. J. & Budarf, M. L. (2001) Genome Res 11, 600-608
Benhamou, Y., Katlama, C., Lunel, F., Coutellier, A., Dohin, E., Hamm, N., Tubiana, R., Herson, S., Poynard, T. & Opolon, P. (1996) Ann. Intern. Med 125, 705-712
Bernard, P. S., Reiser, A. & Pritham, G. H. (2001) in Rapid Cycle Real-Time PCR. Methods and Applications (Meuer, S., Wittwer, C. & Nakagawara, K., eds.), Mutation detection by fluorescent hybridization probe melting curves. pp. 11-19, Springer Verlag, Berlin Heidelberg New York
Bonino, F., Heermann, K. H., Rizzetto, M. & Gerlich, W. H. (1986) J Virol 58, 945-950 Bosserhoff, A. K., Seegers, S., Hellerbrand, C., Scholmerich, J. & Buttner, R. (1999) Biotechniques 26, 1106-1110
Bozdayi, A. M., Bozkaya, H., Turkyilmaz, A. R., Saryodlu, M., Cetinkaya, H., Karayalcin, S., Yurdaydin, C. & Uzunalimoglu, O. (2001) J Clin Virol 21, 91-101
Bozdayi, A. M., Uzunalimoglu, O., Turkyilmaz, A. R., Cinar, K., Sezgin, O., Bozkaya, H., Yurdaydin, C. & Karayalcin, S. (2001) J. Hepatol. 34, 162
Bray, M. S., Boerwinkle, E. & Doris, P. A. (2001) Hum Mutat 17, 296-304
Brow, M. A., Oldenburg, M. C., Lyamichev, V., Heisler, L. M., Lyamicheva, N., Hall, J. G., Eagan, N. J., Olive, D. M., Smith, L. M., Fors, L. & Dahlberg, J. E. (1996) J Clin Microbiol 34, 3129-3137
Cairns, M. J., King, A. & Sun, L. Q. (2000) Nucleic Acids Res 28, E9
Cha, R. S., Zarbl, H., Keohavong, P. & Thilly, W. G. (1992) PCR Methods Appl 2, 14-20
Chen, X. & Kwok, P. Y. (1997) Nucleic Acids Res 25, 347-353
Chen, X., Livak, K. J. & Kwok, P. Y. (1998) Genome Res 8, 549-556
Church, G. M. & Gilbert, W. (1984) Proc Natl Acad Sci USA 81, 1991-1995
Cronin, M. T., Fucini, R. V., Kim, S. M., Masino, R. S., Wespi, R. M. & Miyada, C. G. (1996) Hum Mutat 7, 244-255
Cusi, M. G., Valassina, M. & Valensin, P. E. (1994) Biotechniques 17, 1034-1036
Day, I. N., Spanakis, E., Palamand, D., Weavind, G. P. & O'Dell, S. D. (1998) Trends. Biotechnol. 16, 287-290
De Clercq, E. (1999) Int. J Antimicrob Agents 12, 81-95
De Francesco, L. (1998) The Scientist 12, 16-16

Del Tito BJ, J., Poff, H. E., Novotny, M. A., Cartledge, D. M., Walker, R. I., Earl, C. D. & Bailey, A. L. (1998) Clin Chem 44, 731-739

Delaney, W. E., Edwards, R., Colledge, D., Shaw, T., Torresi, J., Miller, T., Isom, H. C., Bock, T., Manns, M., Trautwein, C. & Locamini, S. (2000) Antiviral Therapy 5, B.64-B.65

Delaney, W. E., Locarnini, S. & Shaw, T. (2001) Antivir. Chem Chemother 12, 1-35

Delaney, W. E., Miller, T. G. & Isom, H. C. (1999) Antimicrob Agents Chemother 43, 2017-2026

Delwart, E. L., Sheppard, H. W., Walker, B. D., Goudsmit, J. & Mullins, J. I. (1994) J Virol 68, 6672-6683

Delwart, E. L., Shpaer, E. G., Louwagie, J., McCutchan, F. E., Grez, M., Rubsamen-Waigmann, H. & Mullins, J. I. (1993) Science 262, 1257-1261

Dienstag, J. L., Schiff, E. & Wright, T. (1998) Gastroenterology 114, A1235

Dienstag, J. L., Schiff, E. R., Wright, T. L., Perrillo, R. P., Hann, H. W., Goodman, Z, Crowther, L., Condreay, L. D., Woessner, M., Rubin, M. & Brown, N. A. (1999) N. Engl. J Med 341, 1256-1263

Drmanac, R., Drmanac, S., Strezoska, Z., Paunesku, T., Labat, I., Zeremski, M., Snoddy, J., Funkhouser, W. K., Koop, B. & Hood, L. (1993) Science 260, 1649-1652

Dubertret, B., Calame, M. & Libchaber, A. J. (2001) Nat. Biotechnol. 19, 365-370

Eis, P. S., Olson, M. C., Takova, T., Curtis, M. L., Olson, S. M., Vener, T. I., Ip, H. S., Vedvik, K. L., Bartholomay, C. T., Allawi, H. T., Ma, W. P., Hall, J. G., Morin, M. D., Rushmore, T. H., Lyamichev, V. I. & Kwiatkowski, R. W. (2001) Nat. Biotechnol. 19, 673-676

Faruqi, A. F., Hosono, S., Driscoll, M. D., Dean, F. B., Alsmadi, O., Bandaru, It, Kumar, G., Grimwade, B., Zong, Q., Sun, Z., Du, Y., Kingsmore, S., Knott, T. & Lasken, R. S. (2001) BMC. Genomics 2, 4

Faudoa, R., Xue, Z., Lee, F., Baser, M. E. & Hung, G. (2000) Hum Mutat 15, 474-478 Fitz, L., Cook, S., Nickbarg, E., Wang, J. H. & Wood, C. R. (1998) BIAjournal 5, 23-25

Fu, L. & Cheng, Y. C. (2000) Antimicrob Agents Chemother 44, 3402-3407

Fu, L., Liu, S. H. & Cheng, Y. C. (1999) Biochem Pharmacol 57, 1351-1359

Ganguly, T., Dhulipala, R., Godmilow, L. & Ganguly, A. (1998) Hum Genet. 102, 549-556

Gerlich, W. & Thomssen, R. (1975) Dev. Biol Stand. 30, 78-87

Gingeras, T. R., Whitfield, K. M. & Kwoh, D. Y. (1990) Ann. Biol Clin (Paris) 48, 498-501

Goldrick, M. M., Kimball, G. R., Liu, Q., Martin, L. A., Sommer, S. S. & Tseng, J. Y. (1996) Biotechniques 21, 106-112

Grange, D. K., Gottesman, G. S., Lewis, M. B. & Marini, J. C. (1990) Nucleic Acids Res 18, 4227-4236

Griffin, T. J., Hall, J. G., Prudent, J. R. & Smith, L. M. (1999) Proc Natl Acad Sci USA 96, 6301-6306

Griffin, T. J. & Smith, L. M. (2000) Trends. Biotechnol. 18, 77-84

Hacia, J. G., Brody, L. C., Chee, M. S., Fodor, S. P. & Collins, F. S. (1996) Nat Genet. 14, 441-447

Hall, J. G., E is, P. S., Law, S. M., Reynaldo, L. P., Prudent, J. R., Marshall, D. J., Allawi, H. T., Mast, A. L., Dahlberg, J. E., Kwiatkowski, R. W., de Arruda, M., Neri, B. P. & Lyamichev, V. I. (2000) Proc Natl Acad Sci USA 97, 8272-8277

Harlow, E. & Lane, D. (1988) Antibodies: A Laboratory Manual. Cold Spring Harbor Laboratory Press, Hawkins, G. A. & Hoffman, L. M. (1999) Electrophoresis 20, 1171-1176

Healey, B. G., Matson, R. S. & Walt, D. R. (1997) Anal. Biochem 251, 270-279

Heermann, K. H., Goldmann, U., Schwartz, W., Seyffarth, T., Baumgarten, H. & Gerlich, W. H. (1984) J Virol 52, 396-402

Hoofnagle, J. H. & Di Bisceglie, A. M. (1993) Prog. Clin Biol Res 382, 337-343

Howell, W. M., Jobs, M., Gyllensten, U. & Brookes, A. J. (1999) Nat. Biotechnol. 17, 87-88

Huber, C. G., Premstaller, A., Xiao, W., Oberacher, H., Bonn, G. K. & Oefner, P. J. (2001) J Biochem Biophys Methods 47, 5-19

Hunt, C. M., McGill, J. M., Allen, M. I. & Condreay, L. D. (2000) Hepatology 31, 1037-1044

Iwahana, H., Fujimura, M., Takahashi, Y., Iwabuchi, T., Yoshimoto, K. & Itakura, M. (1996) Biotechniques 21, 510-519

James, W. & al-Shamkhani, A. (1995) Curr Opin. Biotechnol. 6, 44-49

Jarvis, B. & Faulds, D. (1999) Drugs 58, 101-141

Joung, J. K., Ramm, E. I. & Pabo, C. O. (2000) Proc Natl. Aced Sci USA 97, 7382-7387

Kenney, M., Ray, S. & Boles, T. C. (1998) Biotechniques 25, 516-521 Khanna, M., Park, P., Zirvi, M., Cao, W., Picon, A., Day, J., Paty, P. & Barany, F. (1999) Oncogene 18, 27-38

Khrapko, K., Coller, H., Andre, P., Li, X. C., Foret, F., Belenky, A., Karger, B. L. & Thilly, W. G. (1997) Nucleic Acids Res 25, 685-693

Khrapko, K., Coller, H. A., Li-Sucholeiki, X. C., Andre, P. C. & Thilly, W. G. (2001) Methods Mol. Biol. 163, 57-72

Khrapko, K., Hanekamp, J. S., Thilly, W. G., Belenkii, A., Foret, F. & Karger, B. L. (1994) Nucleic Acids Res 22, 364-369

Kievits, T., van Gemen, B., van Strijp, D., Schukkink, R., Dircks, M., Adriaanse, H., Malek, L., Sooknanan, R. & Lens, P. (1991) J Virol Methods 35, 273-286

Knodell, R. G., Ishak, K. G., Black, W. C., Chen, T. S., Craig, R., Kaplowitz, N., Kiernan, T. W. & Wollman, J. (1981) Hepatology 1, 431-435

Korkko, J., Annunen, S., Pihlajamaa, T., Prockop, D. J. & Ala-Kokko, L. (1998) Proc Natl Acad Sci USA 95, 1681-1685

Kosovsky, M. J., Khaoustov, V. I., Rushton, M. & Yoffe, B. (2000) Biochim Biophys Acta 1490, 63-73

Kristensen, V. N., Kelefiotis, D., Kristensen, T. & Borresen-Dale, A. L. (2001) Biotechniques 30, 318-22, 324, 326

Kwoh, D. Y., Davis, G. R., Whitfield, K. M., Chappelle, H. L., DiMichele, L. J. & Gingeras, T. R. (1989) Proc Natl Acad Sci USA 86, 1173-1177

Lai, C. L., Chien, R. N., Leung, N. W., Chang, T. T., Guan, R., Tai, D. I., Ng, K. Y., Wu, P. C., Dent, J. C., Barber, J., Stephenson, S. L. & Gray, D. F. (1998) N. Engl. J Med 339, 61-68

Langemeier, J. L., Cook, R. F., Issel, C. J. & Montelaro, R. C. (1994) Biotechniques 17, 484-6, 488, 490

Ledford, M., Friedman, K D, Hessner, M. J., Moehlenkamp, C., Williams, T. M. & Larson, R. S. (2000) J. Mol. Diagn. 2, 97-104

Leung, N. (2000) J Med Virol 61, 380-385

Li-Sucholeiki, X. C. & Thilly, W. G. (2000) Nucleic Acids Res 28, E44

Li, Z. & Tyrrell, D. L. (1999) Biochem Cell Biol 77, 119-126

Liaw, Y. F., Chien, R. N., Yeh, C. T., Tsai, S. L. & Chu, C. M. (1999) Hepatology 30, 567-572

Liaw, Y. F., Leung, N. W., Chang, T. T., Guan, R., Tai, D. I., Ng, K. Y., Chien, R. N., Dent, J., Roman, L., Edmundson, S. & Lai, C. L. (2000) Gastroenterology 119, 172-180

Liddle, J. E. & Cryer, A. (1991) A Practical Guide to Monoclonal Antibodies. Wiley, New York Ling, R. & Harrison, T. J. (1999) J. Gen. Virol 80 (PC3), 601-606

Liu, Q., Feng, J. & Sommer, S. S. (1996) Hum Mol. Genet. 5, 107-114

Li; Q., Weinshenker, B. G., Wingerchuk, D. M. & Sommer, S. S. (1998) Biotechniques 24, 140-147

Lizardi, P. M., Guerra, C. E., Lomeli, H., Tussie-Luna, I. & Kramer, F. R. (1988) Biotechnology 6, 1197-1202

Lizardi, P. M., Huang, X., Zhu, Z., Bray-Ward, P., Thomas, D. C. & Ward, D. C. (1998) Nat Genet. 19, 225-232

Lok, A. S. (1994) J. Viral. Hepat. 1, 105-124

Lu, X., Block, T. M. & Gerlich, W. H. (1996) J Virol 70, 2277-2285

Lu, X., Hazboun, T. & Block, T. (2001) Virus Res 73, 27-40

Luo, J., Bergstrom, D. E. & Barany, F. (1996) Nucleic Acids Res 24, 3071-3078

Luscombe, C. A. & Locarnini, S. (1996) Viral hepatitis reviews 2, 1-35

Lyamichev, V., Mast, A. L., Hall, J. G., Prudent, J. R., Kaiser, M. W., Takova, T., Kwiatkowski, R. W., Sander, T. J., de Arruda, M., Arco, D. A., Neri, B. P. & Brow, M. A. (1999) Nat. Biotechnol. 17, 292-296

Machida, A., Kishimoto, S., Ohnuma, H., Baba, K., Ito, Y., Miyamoto, H., Funatsu, G., Oda, K., Usuda, S. & Togami, S. (1984) Gastroenterology 86, 910-918

Markowitz, J. S., Martin, P., Conrad, A. J., Markmann, J. F., Seu, P., Yersiz, H., Goss, J. A., Schmidt, P., Pakrasi, A., Artinian, L., Murray, N. G., Imagawa, D. K., Holt, C., Goldstein, L. I., Stribling, R. & Busuttil, R. W. (1998) Hepatology 28, 585-589

Maxam, A. M. & Gilbert, W. (1977) Proc Natl Acad Sci USA 74, 560-564

Medaglia, M. V., Towler, E. & Fisher, R. J. (1998) BIAjournal 5, 27-27

Mein, C. A., Barratt, B. J., Dunn, M. G., Siegmund, T., Smith, A. N., Esposito, L., Nutland, S., Stevens, H. E., Wilson, A. J., Phillips, M. S., Jarvis, N., Law, S., de Arruda, M. & Todd, J. A. (2000) Genome Res 10, 330-343

Meller, A., Nivon, L., Brandin, E., Golovchenko, J. & Branton, D. (2000) Proc Natl Acad Sci USA 97, 1079-1084

Murakami, A., Nakaura, M., Nakatsuji, Y., Nagahara, S., Tran-Cong, Q. & Makino, K. (1991) Nucleic Acids Res 19, 4097-4102

Myaldshev, M. V., Khripin, Y., Hu, S. & Hamer, D. H. (2001) Genome Res 11, 163-169

Myers, R. M., Fischer, S. G., Lerman, L. S. & Maniatis, T. (1985) Nucleic Acids Res 13, 3131-3145

Myers, R. M., Larin, Z. & Maniatis, T. (1985) Science 230, 1242-1246

Myers, T. W. & Gelfand, D. H. (1991) Biochemistry 30, 7661-7666

Nafa, S., Ahmed, S., Tavan, D., Pichoud, C., Berby, F., Stuyver, L., Johnson, M., Merle, P., Abidi, H., Trepo, C. & Zoulim, F. (2000) Hepatology 32, 1078-1088

Narayanaswami, G. & Taylor, P. D. (2001) Genet Test. 5, 9-16

Nazarenko, I. A., Bhatnagar, S. K. & Hohman, R J (1997) Nucleic Acids Res 25, 2516-2521

Nielsen, P. E. (2001) Curr Med Chem 8, 545-550

Nikiforov, T. T., Rendle, R. B., Goelet, P., Rogers, Y. H., Kotewicz, M. L., Anderson, S., Trainor, G. L. & Knapp, M. R. (1994) Nucleic Acids Res 22, 4167-4175

Nilsson, M., Malmgren, H., Samiotaki, M., Kwiatkowski, M., Chowdhary, B. P. & Landegren, U. (1994) Science 265, 2085-2088

Nishikawa, 3. & Nishihara, T. (1999) BIAjournal 6, 19-21

Nishimura, A. & Tsuhako, M. (2000) Chem. Pharm. Bull. (Tokyo.) 48, 774-778

Ono-Nita, S. K., Kato, N., Shiratori, Y., Masaki, T., Lan, K. H., Carrilho, F. J. & Omata, M. (1999) Hepatology 29, 939-945

Ono-Nita, S. K., Kato, N., Shiratori, Y., Yoshida, H., Kato, J. & Goto, T. (2000) Hepatology 32, 393A Ono, S. K., Kato, N., Shiratori, Y., Kato, J., Goto, T., Schinazi, R. F., Carrilho, F. J. & Omata, M. (2001) J Clin Invest 107, 449-455

Orum, H. & Wengel, J. (2001) Curr Opin. Mol. Ther. 3, 239-243

Paran, N., Geiger, B. & Shaul, Y. (2001) EMBO J. 20, 4443-4453

Pastinen, T., Kurg, A., Metspalu, A., Peltonen, L. & Syvanen, A. C. (1997) Genome Res 7, 606-614

Pastinen, T., Partanen, J. & Syvanen, A. C. (1996) Clin Chem 42, 1391-1397

Pastinen, T., Raitio, M., Lindroos, K., Tainola, P., Peltonen, L. & Syvanen, A. C. (2000) Genome Res 10, 1031-1042

Patolsky, F., Lichtenstein, A. & Willner, I. (2001) Nat. Biotechnol. 19, 253-257

Prince, J. A., Feuk, L., Howell, W. M., Jobs, M., Emahazion, T., Blennow, K. & Brookes, A. J. (2001) Genome Res 11, 152-162

Resch, W., Parkin, N., Stuelke, E. L., Watkins, T. & Swanstrom, R. (2001) Proc Natl Acad Sci USA 98, 176-181

Richman, D. (1996) in Antiviral drug resistance (Richman, D. D., ed.), Antiviral drug resistance: issues and challenges. pp. 1-9, John Wiley and Sons, Chichester Righetti, P. G. & Gelfi, C. (1997) Electrophoresis 18, 1709-1714

Robinson, W. S., Miller, R. H. & Marion, P. L. (1987) Hepatology 7, 64S-73S

Ronaghi, M., Uhlen, M. & Nyren, P. (1998) Science 281, 363, 365

Rowley, G., Saad, S., Giannelli, F. & Green, P. M. (1995) Genomics 30, 574-582

Ruano, G. & Kidd, K. K. (1991) Proc Natl Acad Sci USA 88, 2815-2819

Runnels, L. W. & Scarlata, S. F. (1995) Biophys J 69, 1569-1583

Ryan, D., Nuccie, B. & Aryan, D. (1999) Mol. Diagn. 4, 135-144

Saiki, R. K., Walsh, P. S., Levenson, C. H. & Erlich, H. A. (1989) Proc Natl Acad Sci USA 86, 6230-6234

Sambrook, J., Fritsch, E. F. & Maniatis, T. (1989) Molecular Cloning: A Laboratory Manual. Cold Spring Harbor Laboratory Press, Sanger, F., Nicklen, S. & Coulson, A. R. (1977) Proc Natl Acad Sci USA 74, 5463-5467

Sapolsky, R. J., Hsie, L., Berno, A., Ghandour, G., Mittmann, M. & Fan, J. B. (1999) Genet Anal. 14, 187-192

Sarkar, G., Yoon, H. S. & Sommer, S. S. (1992) Genomics 13, 441-443

Schiff, E., Karayalcin, S. & Grimm, I. (1998) Hepatology 28, 388A

Schinazi, R. (1997) in Viral hepatitis and liver disease (Rizzetto, M., Purcell, R., Gerin, J. & Verme, G., eds.), Impact of nucleosides on hepatitis virus. pp. 736-742, Minerva Medic; Torino Schumm, J. W., Knowlton, R. G., Braman, J. C., Barker, D. F., Botstein, D., Akots, G., Brown, V. A., Gravius, T. C., Helms, C. & Hsiao, K. (1988) Am. J Hum Genet. 42, 143-159

Sheffield, V. C., Cox, D. R., Lerman, L. S. & Myers, R. M. (1989) Proc Natl Acad Sci USA 86, 232-236

Shioda, T., Andriole, S., Yahata, T. & Isselbacher, K. J. (2000) Proc Natl Acad Sci USA 97, 5220-5224

Smith, RD., Cheng, X., Bruce, J. E., Hofstadler, S. A. & Anderson, G. A. (1994) Nature 369, 137-139

Sreevatsan, S., Bookout, J. B., Ringpis, F. M., Pottathil, M. R., Marshall, D. J., de Arruda, M., Murvine, C., Fors, L., Pottathil, R. M. & Barathur, R. R. (1998) J Clin Microbiol 36, 1895-1901

Stary, A., Schuh, E., Kerschbaumer, M., Gotz, B. & Lee, H. (1998) J Clin Microbiol 36, 2666-2670

States, D. J., Gish, W. & Altschul, S. F. (1991) Methods 3, 66-70

Stuyver, L., De Gendt, S., Van Geyt, C., Zoulim, F., Fried, M., Schinazi, R. F. & Rossau, R. (2000) J. Gen. Virol 81 Pt 1, 67-74

Stuyver, L., Wyseur, A., Rombout, A., Louwagie, J., Scarcez, T., Verhofstede, C., Rimland, D., Schinazi, R. F. & Rossau, R. (1997) Antimicrob Agents Chemother 41, 284-291

Stuyver, L., Wyseur, A., van Arnhem, W., Hernandez, F. & Maertens, G. (1996) J Clin Microbiol 34, 2259-2266

Stuyver, L. J., Locamini, S. A., Lok, A., Richman, D. D., Carman, W. F., Dienstag, J. L. & Schinazi, R. F. (2001) Hepatology 33, 751-757

Tassopoulos, N. C., Volpes, R., Pastore, G., Heathcote, J., Buti, M., Goldin, RD., Hawley, S., Barber, J., Condreay, L. & Gray, D. F. (1999) Hepatology 29, 889-896

Taylor, G. R. (1999) Electrophoresis 20, 1125-1130

Tyagi, S., Bratu, D. P. & Kramer, F. R. (1998) Nat. Biotechnol. 16, 49-53

Tyagi, S. & Kramer, F. R. (1996) Nat. Biotechnol. 14, 303-308

Urban, S. & Tyrrell, D. L. (2000) Antiviral Res 45, 185-197

Vijg, J. & van Orsouw, N. J. (1999) Electrophoresis 20, 1239-1249

Vos, P., Hogers, R., Bleeker, M., Reijans, M., van de Lee, T., Hornes, M., Frijters, A., Pot, J., Peleman, J. & Kuiper, M. (1995) Nucleic Acids Res 23, 4407-4414

Wahlestedt, C., Salmi, P., Good, L., Kela, J., Johnsson, T., Hokfelt, T., Broberger, C., Porreca, F., Lai, J., Ren, K., Ossipov, M., Koshkin, A, Jakobsen, N., Skouv, J., Oerum, H., Jacobsen, M. H. & Wengel, J. (2000) Proc Natl Acad Sci USA 97, 5633-5638

Wakefield, J. K., Jablonski, S. A. & Morrow, C. D. (1992) J Virol 66, 6806-6812

Walker, G. T., Little, M. C., Nadeau, J. G. & Shank, D. D. (1992) Proc Natl Acad Sci USA 89, 392-396

Wang, P., Hong, J. H., Cooperwood, J. S. & Chu, C. K. (1998) Antiviral Res 40, 19-44

Whitcombe, D., Theaker, J., Guy, S. P., Brown, T. & Little, S. (1999) Nat. Biotechnol. 17, 804-807

Wittwer, C. (2001) in Rapid Cycle Real-Time PCR. Methods and Applications. (Meuer, S., Wittwer, C. & Nakagawara, K., eds.), Rapid cycle real-time PCR: methods and applications. pp. 1-8, Springer Verlag, Berlin Heidelberg New York Wright, T., Perrillo, R. & Rakela, J. (1997) J Gastroenterol Hepatol 12, A192

Wu, D. Y., Ugozzoli, L., Pal, B. K. & Wallace, R. B. (1989) Proc Natl Acad Sci USA 86, 2757-2760

Xiao, W. & Oefner, P. J. (2001) Hum Mutat 17, 439-474

Xiong, X., Flores, C., Yang, H., Toole, J. J. & Gibbs, C. S. (1998) Hepatology 28, 1669-1673

Xiong, X., Yang, H., Westland, C. E., Das, K., Sarafinos, S. G., Arnold, E. & Gibbs, C. S. (2000) Antiviral Res 46, A56

Yager, T. D., Baron, L., Batra, R., Bouevitch, A., Chan, D., Chan, K., Darasch, S., Gilchrist, R., Izmailov, A., Lacroix, J. M., Marchelleta, K., Renfrew, J., Rushlow, D., Steinbach, E., Ton, C., Waterhouse, P., Zaleski, H., Dunn, J. M. & Stevens, J. (1999) Electrophoresis 20, 1280-1300

Yao, G., Wang, B. & Cui, Z. (1999) Gastroenterology 116, A848

Yeh, C. T., Chien, R. N., Chu, C. M. & Liaw, Y. F. (2000) Hepatology 31, 1318-1326

Zhang, D. Y., Brandwein, M., Hsuih, T. C. & Li, H. (1998) Gene 211, 277-285

---

I claim:

1. A diagnostic kit for detecting resistance to lamivudine or a combination of antiviral drugs comprising lamivudine of an HBV virus present in a biological sample comprising an oligonucleotide capable of discriminating, in said HBV polynucleic acid, a codon at the position corresponding to position 204 of sequence P7RT (position 108 of SEQ ID NO:4) encoding a serine from a codon at the position corresponding to position 204 of sequence P7RT (position 108 of SEQ ID NO:4) encoding a methionine, valine or isoleucine.

2. The diagnostic kit according to claim 1 further comprising an oligonucleotide capable of discriminating, in said HBV polynucleic acid, a codon at the position corresponding to position 180 of sequence P7RT (position 84 of SEQ ID NO:4) encoding a methionine from a codon at the position corresponding to position 180 of sequence P7RT (position 84 of SEQ ID NO:4) encoding a leucine.

3. The diagnostic kit according to claim 1 wherein said oligonucleotide is attached or immobilized to a solid support.

4. The diagnostic kit according to claim 2 wherein at least one of
said oligonucleotide capable of discriminating, in said HBV polynucleic acid, a codon at the position corresponding to position 204 of sequence P7RT (position 108 of SEQ ID NO:4) encoding a serine from a codon at the position corresponding to position 204 of sequence P7RT (position 108 of SEQ ID NO:4) encoding a methionine, valine or isoleucine is attached or immobilized to a solid support and
said oligonucleotide capable of discriminating, in said HBV polynucleic acid, a codon 180 encoding a methionine from a codon 180 encoding a leucine is attached or immobilized to a solid support.

* * * * *